United States Patent
Towler et al.

(10) Patent No.: US 9,186,107 B2
(45) Date of Patent: *Nov. 17, 2015

(54) METHODS FOR ASSESSING RISK OF BONE FRACTURE

(71) Applicant: Crescent Diagnostics Limited, London (GB)

(72) Inventors: Mark Robert Towler, Annacotty (IE); Ernest Poku, London (GB)

(73) Assignee: Crescent Diagnostics Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,316

(22) Filed: Jun. 19, 2014

(65) Prior Publication Data
US 2015/0072434 A1  Mar. 12, 2015

Related U.S. Application Data

(63) Continuation of application No. 13/301,952, filed on Nov. 22, 2011, now abandoned, which is a continuation-in-part of application No. 11/570,669, filed as application No. PCT/EP2005/006694 on Jun. 20, 2005, now Pat. No. 8,535,238.

(60) Provisional application No. 60/581,807, filed on Jun. 22, 2004.

(51) Int. Cl.
*A61B 6/00* (2006.01)
*A61B 5/00* (2006.01)
*G01N 33/68* (2006.01)
*G01N 21/65* (2006.01)

(52) U.S. Cl.
CPC ............ *A61B 5/4504* (2013.01); *A61B 5/0075* (2013.01); *A61B 5/4869* (2013.01); *A61B 5/7275* (2013.01); *G01N 21/65* (2013.01); *G01N 33/68* (2013.01)

(58) Field of Classification Search
CPC .. A61B 5/4504; A61B 5/0075; A61B 5/4869; A61B 5/7275; G01N 33/68; G01N 21/65
USPC ............................................ 436/86; 600/477
See application file for complete search history.

(56) References Cited

U.S. PATENT DOCUMENTS

2002/0002336 A1* 1/2002 Marchitto et al. ............ 600/473
2002/0127711 A1* 9/2002 Kale et al. ..................... 435/325

OTHER PUBLICATIONS

Hansen et al., The Mechanical Properties of Skin in Osteogenesis Imperfecta, Arch Dermatol. 2002;138:909-911.*
Robson, Hardness of finger nails in well-nourished and malnourished populations, Br J Nutr. Sep. 1974;32(2):389-394.*
WHO Technical Report Series, Prevention and Management of Osteoporosis.*
MSM, http://www.msmforless.com/benefits_msm.htm, Feb. 25, 2002.*
Williams et al., Raman Spectra of Human Keratotic Biopolymers: Skin, Callus, Hair and Nail, Journal of Raman Spectroscopy, vol. 25, 95-98 (1994).*
Tarnowski et al., Mineralization of Developing Mouse Calvaria as Revealed by Raman Microspectroscopy, American Society for Bone and Mineral Research, Journal of Bone and Mineral Research, vol. 17, No. 6, 2002.*

* cited by examiner

*Primary Examiner* — Bo J Peng
(74) *Attorney, Agent, or Firm* — Brown Rudnick LLP; Thomas C. Meyers

(57) ABSTRACT

The invention generally relates to methods for assessing risk of bone fracture. In certain embodiments, methods of the invention involve a) conducting an assay to determine a characteristic of keratinized tissue obtained from a mammal, b) analyzing at least one bone-fracture risk factor associated with the mammal, and c) correlating results from steps (a) and (b), thereby assessing the risk of bone fracture of a bone of the mammal.

10 Claims, 8 Drawing Sheets

METHODS FOR ASSESSING RISK OF BONE FRACTURE

RELATED APPLICATIONS

The present application is a continuation of U.S. patent application Ser. No. 13/301,952, filed Nov. 22, 2011, which is a continuation-in-part of U.S. patent application Ser. No. 11/570,669, filed Sep. 11, 2007, which is a U.S. national phase application of PCT/EP05/06694, filed Jun. 20, 2005, which claims the benefit of and priority to U.S. provisional application Ser. No. 60/581,807, filed Jun. 22, 2004, the content of each of which is incorporated by reference herein in its entirety.

FIELD OF THE INVENTION

The invention generally relates to methods for assessing risk of bone fracture.

BACKGROUND

Osteoporosis is a disease characterized by a deficiency of bone that affects both the protein matrix and the mineral fraction, resulting in a decrease in the resistance of bones to fracture. Osteoporosis is generally diagnosed by means of dual energy x-ray absorptiometry (DEXA), which provides a quantitative measurement of the amount of mineral present in bone and allows determination of fracture risk at a measured site. A decrease in bone mineral density (BMD) as measured by DEXA is indicative of osteoporosis and increased risk of fractures. See, for example, Nevitt and Cummings (1993) J. Am. Geriatr. Soc. 41:1226; and Parfitt (1993) Calcif. Tissue Int. 53:S82.

While bone densitometry is the current gold standard for diagnosis of bone diseases such as osteoporosis, this method is limited to measuring bone mass, and it does not take into consideration the microarchitecture of the bone, the crystal organization, size and shape, the connectivity of the trabecullar network, and the structure of the bone proteins. Further, the lack of perfect correlation between bone mineral density and bone fractures suggests that low bone mineral density is not the only cause of fragile bones (Ott (1993) Calcif. Tissue Int. 53(Suppl.):S7). Thus, while the degree of mineralization is the current standard by which osteoporosis is diagnosed, it is unable to detect bone fragility due to deficiency in protein matrix.

Moreover, DEXA is a relatively expensive diagnostic procedure that exposes the patient to potentially harmful x-rays; thus it cannot be used for mass screenings, such as at routine checkups. Therefore, it is possible that clinicians will under diagnose patients at risk for fracture because the bone disease is often unrecognized until a fracture occurs, or because bone mineral density does not always correlate with a risk of fragile bones even when DEXA is used. The alternative of obtaining collagen from a patient's bones is an even more expensive and risky procedure. Thus, clinicians need new, low-risk methods to diagnose patients that are at an increased risk of bone fracture.

SUMMARY

Methods of the invention combine analytical measurements with other clinical risk factors to improve overall predictive performance of diagnostics for assessing risk of bone fracture. Thus, in addition to looking at analytical measurements, methods of the invention combine the analytical measurements (e.g., physical or chemical changes in keratinized tissue) with bone-fracture risk factors (e.g., age, sex, weight, height, previous fracture, parental hip fracture, current smoking, glucocorticoids, rheumatoid arthritis, secondary osteoporosis, or alcohol consumption) to provide an additional level of clinical clarity. For example, analytical measurements discussed below may provide information about a disposition toward bone fracture. Inn certain cases, the analytical measurement is enhanced by combining it with bone-fracture risk factors. Thus, methods of the invention provide for a combination of analytical measurements in combination with bone-fracture risk factors in order to assess risk of bone fracture.

Methods of the invention involve conducting an assay to determine a characteristic of keratinized tissue obtained from a mammal, analyzing at least one bone-fracture risk factor associated with the mammal, and correlating results from the conducting step and the analyzing step to thereby assess the risk of bone fracture of a bone of the mammal.

Numerous assays may be used to determine a characteristic of keratinized tissue, particularly a physical or chemical change in the keratinized tissue, e.g., nail, hair, or skin. Keratinized tissue may be obtained by any clinically acceptable methods known in the art. In certain embodiments, the keratinized tissue is a clipped finger nail or toe nail. In particular embodiments, the clipped finger nail or toe nail has been archived for a period of time.

Exemplary assays include measuring changes in hardness of the tissue, measuring changes in modulus of the tissue, and measuring chemical changes in the tissue, such as levels of sulfur bonding. These assays may be performed by numerous different techniques, such as nanoindentation, atomic force microscopy, Raman spectroscopy, nuclear magnetic resonance spectroscopy, Fourier transform infrared spectroscopy, chiroptical techniques, mass spectrometry, chromatography, and reactions with Elman's reagent. These assays may be performed in situ or on collected keratinized tissue samples. In certain embodiments, methods of the invention may take the measurement at a depth of at least 50 microns into the tissue.

In certain embodiments, nanoindentation is used to measuring changes in hardness or changes in modulus of the tissue. In other embodiments, Raman spectroscopy is used to measure changes in the chemical composition of the tissue. An exemplary change to be measured is changes in levels of sulfur bonding in proteins in the tissue. Generally, the Raman spectroscopy measures a peak in a 0-4000 $cm^{-1}$ spectral region. In particular embodiments, the Raman spectroscopy measures a peak at about 510 $cm^{-1}$, a peak at about 621 $cm^{-1}$, or a peak at about 643 $cm^{-1}$.

In addition to looking at analytical measurements, methods of the invention combine the analytical measurements (e.g., physical or chemical changes in keratinized tissue) with bone-fracture risk factors. Exemplary bone-fracture risk factors include age, body mass index (BMI), smoking status, thyroid hormone use, diet, age at menopause, alcohol consumption, and diagnosis of osteoporosis. In certain embodiments, only a single risk factor is analyzed. In other embodiments, a combination of risk factors are analyzed.

Methods of the invention may be used to assess the risk of bone fracture in any mammal. Methods of the invention are particularly useful for assessing the risk of bone fracture, in a human female (e.g., a woman under 65 years old or a woman over 65 years old), especially a post-menopausal human female.

Another aspect of the invention provides methods for assessing risk of bone fracture of a bone of a mammal that involve measuring changes in chemical composition of keratinized tissue by a Raman spectroscopy technique, and comparing obtained Raman spectra to a set of reference spectra, thereby assessing the risk of bone fracture of a bone of the mammal. The reference set includes spectra from diseased and non-diseased keratinized tissue samples. The obtained spectra is compared to this reference set, and matching of the obtained spectra with the known reference (i.e., diseased or non-diseased) allows one to assess risk of bone fracture.

DETAILED DESCRIPTION

Figure 1:
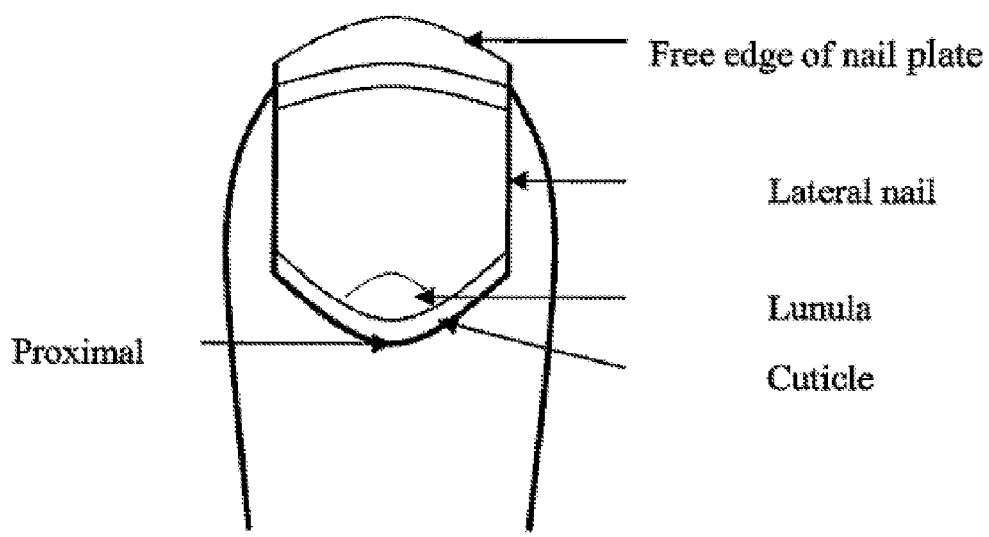
FIG. 1 shows a schematic of a human fingernail. The nail clippings used in Example 1 described herein were taken from the free edge of the nail plate.

Bone is a composite material, including mineral, organic, and water phases (Katz (1971) J. Biomech. 4:455). The mineral phase, mainly hydroxyapatite (HA), imparts compressive strength, while the organic phase, collagen, imparts flexibility. Wang et al. (1998) Bone 23:67 have shown that with increasing age, the fracture toughness of bone is decreased and its microhardness increased without significant changes in BMD. McCalden et al. reported similar findings, indicating that even without significant changes in BMD, the tensile strength of bone can decrease with age due to increased porosity (McCalden et al. (1993) J. Bone Joint Surg. 75A: 1193). There is now a belief that the organic phase of bone plays a significant role in osteoporosis. Kovach et al. have shown that changes in the structural characteristics of the collagen network detected using a laser fluorescence technique correlate significantly with bone fracture toughness (Kovach et al. (1997) Proceedings of the 43th Annual Meeting of the Orthopaedic Research Society, San Francisco, Calif., 22:37). This work is supported by other findings demonstrating that the organic phase of bone is responsible for much of its ability to resist fracture (Wang et al. (1998) Proceedings of the 44th Annual Meeting of the Orthopaedic Research Society, New Orleans, La.; and Wang et al. (2002) Bone 31:1). Mansell and Bailey found that collagen in osteoporotic bone is not normal but instead contains higher levels of lysine hydroxylation and modified cross-linking (Mansell and Bailey (2003) Int. J. Biochem. Cell Biol. 35:522). This and other studies have shown that osteoporosis has a degenerative effect on protein production in bones with increased immature collagen cross-links, increased collagen synthesis and degradation (increased turnover despite overall loss of collagen), as well as reduced mineralization (Oxlund (1996) Bone 19:479; and Bailey (2002) J. Musculoskel. Neuron Interact. 2:529). The increased hydroxylation leads to the formation of finer fibrils with altered crosslinks, and reduced calcification, which further contributes to the fragility of the bone.

The invention generally relates to methods for assessing risk of bone fracture. In certain embodiments, methods of the invention involve conducting an assay to determine a characteristic of keratinized tissue obtained from a mammal, analyzing at least one bone-fracture risk factor associated with the mammal, and correlating results from steps conducting step and the analyzing step to thereby assess the risk of bone fracture of a bone of the mammal.

Assays to Determine a Characteristic of Keratinized Tissue

Assays to determine characteristics of keratinized tissue are described for example in Towler et al. (U.S. patent application number 2009/0099458) and Carron et al. (U.S. patent application number 2009/0012403), the content of each of which is incorporated by reference herein in its entirety. Assays of the invention detect physical and chemical changes in keratinized tissue that are predictive of the presence of a bone disease that is associated with a change in bone elasticity or bone density. The physical and chemical changes include a reduction in the hardness of a keratinized tissue, a reduction in the modulus of a keratinized tissue, or a reduction in the level of sulfur bonding in a keratinized tissue. Methods of detecting changes in the hardness and modulus of keratinized tissue include measuring the nanoindentation pressure and deformation of a keratinized tissue such as nail, hair, or skin. Methods of detecting changes in the level of sulfur bonding in keratinized tissue include using spectral analysis such as Raman spectroscopy to identify the relative abundance of disulfide bonds and carbon sulfide bonds in a keratinized tissue such as nail, hair, or skin. In certain embodiments, a whole spectrum analysis using Raman spectroscopy is performed. The advantages of examining a keratinized tissue such as nail, hair, or skin lies in the ability to assess properties other than those measured by standard bone densitometry, the ease of access to such samples, and the rapid growth of keratinized tissue, which allows changes to be monitored on a more frequent basis.

Without being bound by any mechanism or theory of action, it has been found that physical and chemical changes within a keratinized tissue correlate to the presence or absence of bone disease that is associated with changes in bone elasticity or bone density, such as osteoporosis. A bone disease that is associated with changes in bone elasticity or bone density includes any disease where the risk of bone fracture is increased due to structural and chemical changes in the bone. Examples of such diseases include but are not limited to osteoporosis, osteogenesis imperfecta, Paget's disease, and the like. These structural and chemical changes in bone are measurable by any means known in the art including but not limited to measurement of bone mineral density (BMD) and bone biopsy. The structural and chemical changes in bone correlate to changes in the chemical composition of a keratinized tissue or changes in the hardness or modulus of such keratinized tissue. In particular embodiments, the structural and chemical changes in bone correlate to changes in the level of sulfur bonding of a keratinized tissue or changes in the hardness or modulus of such keratinized tissue.

Keratinized tissue includes any biological sample having the protein keratin, more particularly hard keratin. Keratinized tissue includes nail (fingernails and toenails), hair, skin (i.e., epidermis), and the like. Measurements on keratinized tissue samples may be made in situ (e.g., measurements made on the attached nail, hair, or skin sample, including but not limited to skin on the hand, foot, arm, leg, torso, or face) or by collecting the keratinized tissue sample (e.g., as clipped nails (also referred to as nail clippings), clipped hair, detached skin (i.e., epidermal peels or scrapings)) for measurement at a later time. The safety of obtaining keratinized tissue samples such as nail, hair, or skin, coupled with their diagnostic power independent of bone mineral density and bone biopsy make keratinized tissue-based diagnostic assays a useful new clinical tool.

Assays of the invention are able to detect changes in the physical or chemical structure of the keratinized tissue sample and correlating a change (or lack of change) with a diagnosis of bone disease. In some embodiments, the changes in physical or chemical structure of a keratinized tissue sample are used to assess whether the subject has osteoporosis or other bone disease that is associated with changes in bone elasticity or bone density and, thus, is at increased risk of bone fractures.

In other embodiments, the changes in physical or chemical structure of a keratinized tissue sample are used to assess the prognosis of a subject with osteoporosis or other bone disease that is associated with changes in bone elasticity or bone density. Because the presence or absence of reduced bone mineral density is not in perfect correlation with the risk of bone fracture, changes in the physical or chemical structure of keratinized tissue may be used to assess additional risk factors such as correlating the likely progression of disease and prognosis of a subject at increased risk of fracture.

Physical and chemical markers of interest include changes in the hardness or modulus of a keratinized tissue or changes in the level of sulfur bonding within the keratinized tissue. Methods for detecting changes in hardness or modulus of a keratinized tissue are well known in the art and include but are not limited to nanoindentation and atomic force microscopy. Methods for detecting changes in the level of sulfur bonding within a keratinized tissue are also well known in the art and include but are not limited to Raman spectroscopy, nuclear magnetic resonance spectroscopy, Fourier transform infrared (FT-IR) spectroscopy, chiroptical techniques, mass spectroscopy, chromatography, reaction with other chemicals such as Elman's reagent, and the like. See, for example, Walker (2002) The Protein Protocols Handbook (Humana Press, Totowa). Those skilled in the art recognize that the diagnostic power of the variables disclosed herein is not limited to a particular method of detection of the variable or changes thereof.

Keratin molecules are helical and fibrous. They form intermediate filaments by twisting around each other to form strands. Keratin contains a high percentage of sulfur-containing amino acids, largely cysteine. These cysteines form disulfide bridges between the individual molecules. The bridges cross-link the various secondary, tertiary, and quaternary keratin structures and thereby help maintain the structural rigidity of keratinized tissue. Hard keratin, such as that in hair, nails, and skin (particularly the epidermal layer) has a greater amount of structural rigidity due to more disulfide bonds.

As discussed herein, changes in hardness, modulus, or level of sulfur bonding of a keratinized tissue are correlated to bone disease. Therefore, changes in these physical and chemical properties of keratinized tissue may be used as diagnostic markers for bone diseases that are associated with changes in bone elasticity and bone density. In one embodiment of the invention, a change in the hardness of a keratinized tissue is used to diagnose a patient with bone disease. In other embodiments, a change in the modulus of a keratinized tissue is used to diagnose bone disease. In yet other embodiments, a change in the level of sulfur bonding in a keratinized tissue is used to diagnose bone disease. In yet other embodiments, a change in whole spectra analysis using a principle component analysis, a independent component analysis, or a combination thereof links to a percentage of fracture risk.

Modulus and hardness are measures of the brittleness of a keratinized tissue, for example, nails, hair, or skin. Modulus refers to stiffness or resistance of a keratinized tissue sample to deformation. Hardness refers to the extent to which a keratinized tissue sample is resistant to pressure. Level of sulfur bonding refers to the extent of the reduction (or, reciprocally, oxidation) of sulfur-containing amino acids such as cysteine and methionine, more specifically the extent to which the proteins form disulfide bridges or carbon sulfide bonds.

The presence, absence, or extent of change in hardness, modulus, or level of sulfur bonding of a keratinized tissue sample, such as nails, hair, or skin, can be correlated to the presence, absence, or extent of bone disease using methods standard in the art. See, for example, Zhou et al. (2002) Statistical Methods in Diagnostic Medicine (Wiley, New York), the content of which is incorporated by reference herein in its entirety. In one embodiment, the hardness of a keratinized tissue such as nails, hair, or skin provides a diagnostic criterion for bone fragility and osteoporosis. In another embodiment, the modulus of a keratinized tissue such as nails, hair, or skin provides a diagnostic criterion for bone fragility and osteoporosis. In other embodiments, the level of sulfur bonding within a keratinized tissue such as nails, hair, or skin provides a diagnostic criterion for bone fragility and osteoporosis. In further embodiments, the hardness, the modulus, or the level of sulfur bonding in a keratinized tissue such as nails, hair, or skin is used in combination with other diagnostic criteria previously known in the art such as bone mineral density tests (e.g., DEXA scans) and other previously known clinical correlates to disease. As previously noted, measurements on keratinized tissue samples may be made in situ (e.g., measurements made on the attached nail, hair, or skin sample) or by collecting the keratinized tissue sample (e.g., as clipped nails (also referred to as nail clippings), clipped hair, detached skin (i.e., epidermal peels or scrapings)) for measurement at a later time.

In one embodiment, the hardness or modulus of a keratinized tissue sample is measured by a nanoindentation method using a machine previously described by Arteaga et al. (1993) Tribology Int'l. 26:305, the content of which is incorporated by reference herein in its entirety. In this method, force is applied to a keratinized tissue sample and the resistance measured. In one such embodiment, the keratinized tissue sample is nails (fingernails or toenails), either attached (i.e., measurement performed in situ) or clipped. Where nail clippings are to be measured, the nail clippings are collected from the free edge of the nail plate as shown in FIG. 1. Following collection, nanoindentation is used to detect hardness or modulus of the nail clippings. Preferably the nail clippings are subjected to nanoindentation within 1 day to within one month of collection, more preferably within 1 day to within three weeks of collection. In some embodiments, the nail clippings are subjected to nanoindentation within 1 day to within two weeks of collection; in other embodiments, the nail clippings are subjected to nanoindentation within 1 day to within one week, preferably within 1 day to within 3 days of collection. Where nail clippings are to be stored for future analysis, they are collected and stored in sealed jars to minimize changes in hydration following nail clipping collection.

Following collection of the nail clippings, the clippings are subjected to nanoindentation to assess hardness and modulus of this keratinized tissue. More specifically, pressure and release cycle readings are taken of the displacement of the indenter $\delta$, and the load P, allowing the examination of force-penetration data during both the loading and unloading phases. A curve measuring the penetration depth at each force level during the loading and unloading phases can then be generated.

Figure 2:
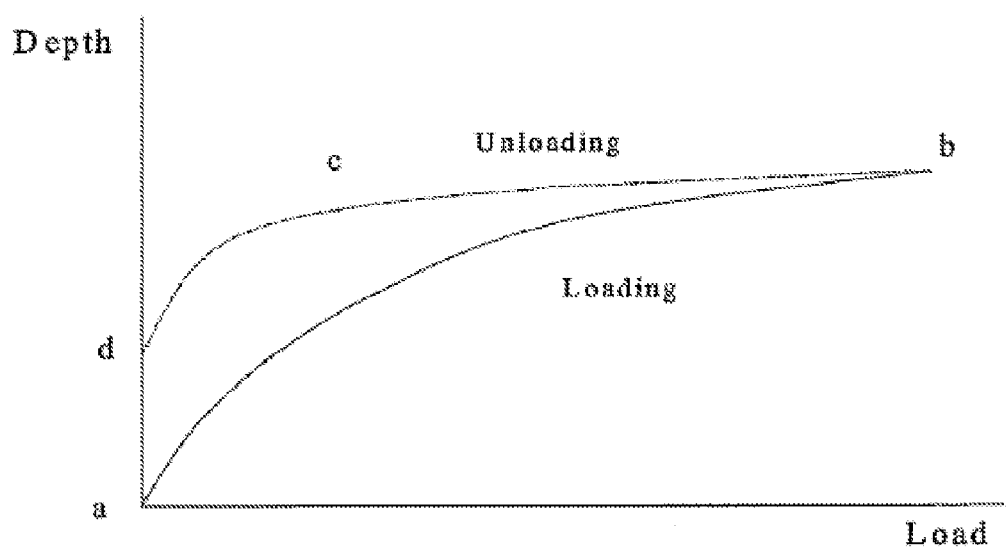
FIG. 2 shows a schematic representation of a typical nanoindentation curve comprising loading (a-b) and unloading (b-c-d) phases.

In this manner, the modulus can be defined as the linear section of the nanoindentation unloading curve (b-c in FIG. 2).

In some embodiments, the hardness, H, is defined as $$H=P/A \quad \text{(Formula 1)}$$

where P is the force applied to the indenter and A is the projected area of the contact. In nanoindentation, the projected area of contact is calculated from the geometry of the indenter and the measured depth of penetration in contact with the indenter, h, using the machine disclosed by Arteaga et al. (1993) Tribology Int'l. 26:305, where $$A=kh^2 \quad \text{(Formula 2)}$$

and where k is a constant dependant upon the geometry and type of indenter used. In some embodiments, the indenter is a trigonal diamond pyramid with an equilateral triangular cross-section and a 90° angle between each face and the opposing edge (the corner of a cube). For this indenter k=2.6. Substituting (Formula 2) into (Formula 1) gives:

$$H=P/2.6\times\delta_p^2 \quad \text{(Formula 3)}$$

While the indenter is moving into the material, the load P has to provide the stress field which is necessary to support the plastic flow of material out of the indentation as well as the static pressure equal to the hardness. Due to this, the curve of dynamic hardness as a function of depth derived from (Formula 1) usually has a very high value at small depths where the strain rate, which is proportional to $1/\delta \, d\delta/dt$, is greatest. In some embodiments, a single hardness number is quoted from the results and this is taken as the maximum applied force where the strain rate is a minimum.

Though the foregoing discussion of nanoindentation is directed to nail clippings, the methodology is also applicable to attached nails, as well as to other keratinized tissues including hair and skin, which can be measured in situ or on collected tissue samples that are handled in a manner similar to that described above for nail clippings. In this manner, keratinized tissue is collected, for example, clipped hair or detached skin tissue, and the collected tissue sample is subjected to nanoindentation within 1 day to within one month of collection, more preferably within 1 day to within three weeks of collection. In some embodiments, the keratinized tissue is collected and the collected tissue sample is subjected to nanoindentation within 1 day to within two weeks of collection; in other embodiments, the keratinized tissue is collected and the collected tissue sample is subjected to nanoindentation within 1 day to within one week, preferably within 1 day to within 3 days of collection. As previously noted above for nail clippings, where keratinized tissue is to be stored for future analysis, tissue samples are collected and stored in sealed jars to minimize changes in hydration following tissue collection.

In another embodiment, level of sulfur bonding within a keratinized tissue such as nails, hair, or skin is measured, either in situ or following collection of the keratinized tissue sample. Of particular interest is the extent of disulfide bridge formation between cysteine molecules in the keratinized tissue. The extent of crosslinking of cysteine via oxidized thiols (also known as the formation of cystine) correlates with the hardness or modulus of keratinized tissue as discussed supra. In one such embodiment, the extent of disulfide bridge formation is measured by means of spectral analysis, for example, using Raman spectroscopy, nuclear magnetic resonance spectroscopy, FT-IR spectroscopy, chiroptical techniques, mass spectroscopy, chromatography, reaction with other chemicals such as Elman's reagent, and the like.

Raman spectroscopy is a widely used tool for qualitative and quantitative analysis of materials. It relies on a spectral shift that occurs when light is projected onto a material to be tested and then deflected off the material surface. In laser Raman spectroscopy, monochromatic laser light that is deflected or scattered off the test material surface is detected by a sensitive detection system. The majority of the light deflected off the surface is scattered elastically at the same wavelength as the original light source in a process known as Rayleigh scattering. The remainder of the deflected light is scattered inelastically at a wavelength that differs from the original light source in a process known as Raman scattering. The two types of scattered light are separated from each other using any suitable wavelength selection system, such as prisms, filters, or optical gratings. The resulting Raman spectrum can be used to identify and quantify concentrations of various substances within the test material of interest. Raman scattering detected from a keratinized tissue sample can be used to identify individuals having or at risk of developing a bone disease such as osteoporosis.

Methods of the invention may be conducted using any Raman spectroscopy technique or any technique that produces Raman spectra. Exemplary techniques include back-scattering Raman spectroscopy, offset Raman spectroscopy (SORS), Transmission Raman spectroscopy (Anal. Che., 80(21):8146-8152, 2010), Coherent Anti-Stokes Raman spectroscopy (CARS), Surface Enhanced Raman spectroscopy (SERS), and Resonance Raman spectroscopy (UV or visible).

In this manner, a keratinized tissue sample, such as nail (i.e., fingernail or toenail), hair, or skin (measured in situ or on a tissue sample collected as described above) is irradiated by a light source such as a laser, and then the wave number and intensity of the inelastically scattered light is measured. In one embodiment, the keratinized tissue sample is nail. Raman spectra of human nails are known (Akhtar and Edwards (1997) Spectrochimica Acta A53:81; and Edwards et al. (1998) Spectrochimica Acta A54:745), the content of each of which is incorporated by reference herein in its entirety. The Raman spectra reflect the bonding arrangements in the molecular makeup of a keratinized tissue such as nail, hair, or skin. Although the Raman spectrum can cover between 300 cm$^{-1}$ and 1800 cm$^{-1}$, particular peaks in this spectrum correspond to specific chemical structures of interest to the methods of the present invention. For sulfur bonding, the area of interest is generally between 400 cm$^{-1}$ and 700 cm$^{-1}$. For example, in human nails, three peaks correspond to sulfur bonds present in keratin, the most abundant protein in nails, specifically the disulfide bond (S—S, gauche-gauche-gauche conformation) at 510 cm$^{-1}$ and the carbon sulfide bond (C—S) at about 621 cm$^{-1}$ and 643 cm$^{-1}$. These Raman spectra can be used alone or in combination to indicate the extent to which cysteine is oxidized to form disulfide bridges in a keratinized tissue sample.

Thus, in some embodiments, the Raman spectra measurements are conducted on nails (i.e., fingernails or toenails) in situ or on nail clippings. Any Raman spectroscopy apparatus known in the art can be used to analyze the nails. See, for example, the non-invasive Raman spectroscopy apparatus for in situ measurements of carotenoid levels in living tissues described in U.S. Pat. Nos. 5,873,831 and 6,205,354, herein incorporated by reference in their entirety, and a modification of this apparatus as described in Example 3 herein below. Such an apparatus specifically designed for non-invasive measurement of sulfide bond levels in a keratinized tissue sample such as nails, particularly the level of disulfide bonding corresponding to the peak appearing at 510 cm$^{-1}$ of the Raman spectrum, comprises the following components: (1) a means for generating light within a wavelength giving a Raman response with a wavelength shift for the disulfide bond to be detected; (2) a delivery means for directing this light onto the fingernail, where this light has an intensity that does not damage the fingernail and does not alter disulfide bond levels; (3) a collection means for collecting light scattered from the fingernail; (4) spectrally selective means for selecting Raman shifted light from the scattered light collected by the collection means; (5) detection means for scanning and measuring the Raman shifted light at frequencies characteristic of disulfide bonds; and (6) quantifying means for determining Raman signal intensity for the disulfide bonds.

As the Raman shift is independent of the wavelength of incident light used, any strong and fairly monochromatic light source can be used in this technique. Thus, for example, the means for generating light can be a laser light source; alternatively, other means include, but are not limited to, light sources that generate monochromatic light, and any other light projection system. Various delivery means and collection means can be used, including, for example, optical components for directing a beam of light from the light source to the nail to be measured, either in situ or as a nail clipping, and for collecting the scattered light. The collected scattered light can be spectrally selected, for example, using a Raman spectrometer that separates the Raman scattered light from Rayleigh scattered light. Thus, the spectrally selective system can comprise various optical components, including, but not limited to, prisms, grating monochromators, and filters such as holographic filters, dielectric filters, acousto-optic filters, combinations thereof, and the like. The light detection system is capable of measuring the intensity of the Raman scattered light as a function of frequency in the frequency range of interest, i.e., at 510 cm.sup.-1 for detecting the level of disulfide bonding in the nail sample. Components within the light detection system include, but are note limited to, a photomultiplier apparatus, photodiodes, devices such as a charge coupled device (CCD) detector array, an intensified CCD detector array, and the like. Preferably the light detected by the light detection system is converted into a signal that can be displayed visually, for example, on a computer monitor or the like, or is converted into other digital or numerical formats. The resultant Raman signal intensities are preferably analyzed via a quantifying means such as a quantifying system, which may be calibrated, for example, by comparison with spectra obtained from other samples of interest or other peaks on the same sample. In some embodiments, the quantifying system is a computer that comprises spectral data acquisition software installed so that spectral analysis can be manipulated, for example, to remove background noise and the like. For further details on exemplary components that can be included in a Raman spectroscopy apparatus for measurements of level of sulfur bonding, particularly disulfide bonding, in keratinized tissue samples in situ, see U.S. Pat. Nos. 5,873,831 and 6,205,354, herein incorporated by reference in their entirety.

Figure 11:
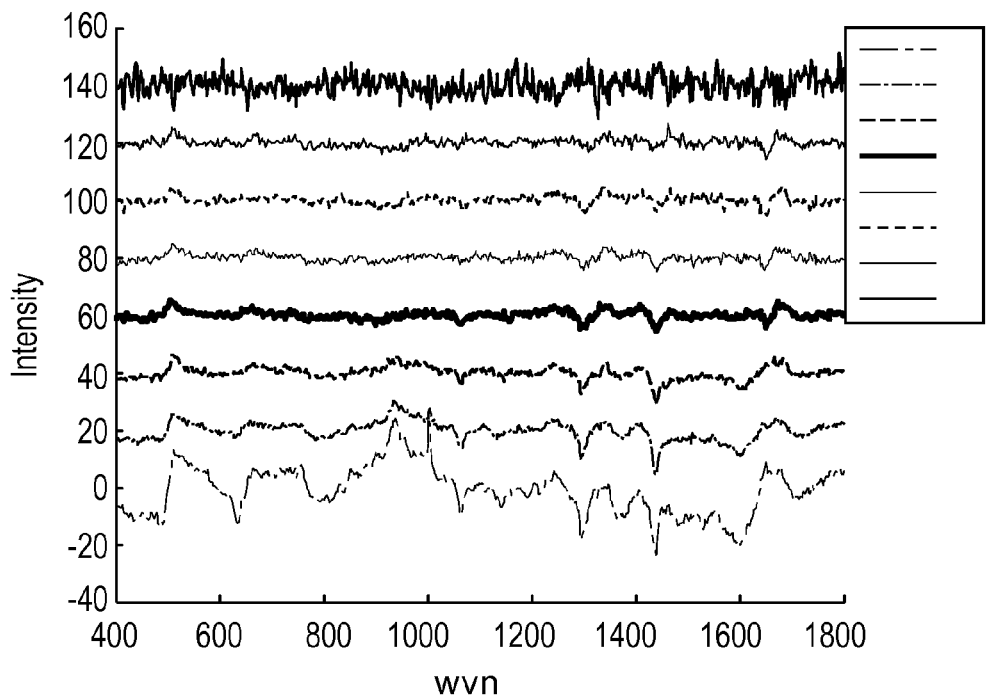
FIG. 11 is a graph showing differences between Raman spectra obtained at different nail depths.
Figure 12:
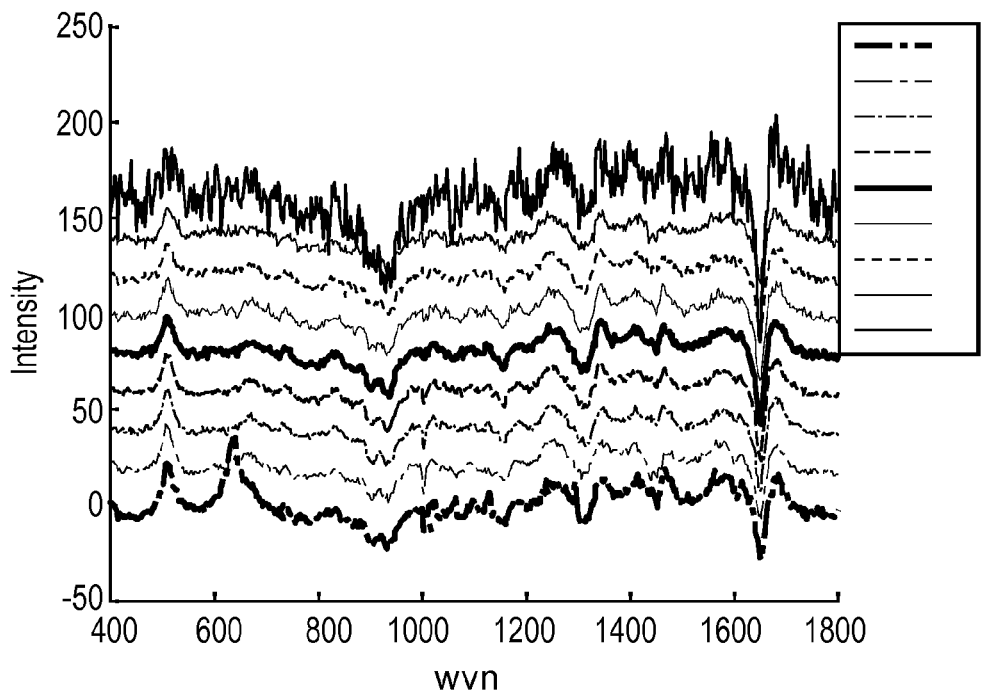
FIG. 12 is a graph showing differences between the two groups, per depth.
Figure 13:
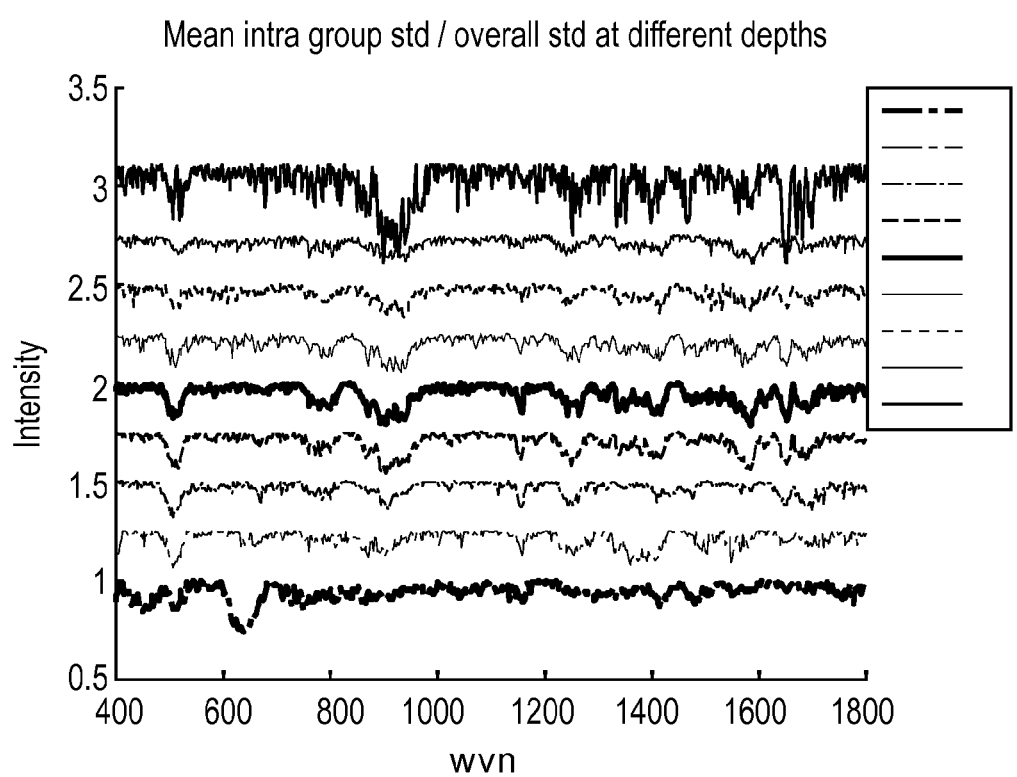
FIG. 13 is a graph showing the mean intra group standard deviation divided by the overall standard deviation.

In particular embodiments, the measurement is obtain at a depth of 50 microns into the tissue. The depth dependent spectral differences between fracture and non fracture nails was investigated using nail depth profiles between 0 and 80 micron. Depth spectra were obtained from 6 nails, 3 non-fractured and 3 fractured. FIG. 11 shows the differences between subsequent depths. The difference is one depth average minus the next depth average, where the spectra are average per depth (not per group). From this figure it is clear that the least differences are in the depth range of 30-70 µm. FIG. 12 shows the differences between the two groups, per depth. In this figure it can also be seen that the difference is consistent in the depth range 30-70 µm. FIG. 13 shows the mean intra group standard deviation divided by the overall standard deviation. This is a measure for how good the groups can be separated at a certain wavenumber interval: the lower this value, the better the two groups can be separated. If the overall standard deviation is the same as the mean intra group standard deviation the groups must be highly overlapping, and adding them will give no increase in the standard deviation. If the overall standard deviation is larger than the mean intra group standard deviation the groups must be separated from each other, and adding them will give an increase in the standard deviation.

In another embodiment, spectral analysis of obtained Raman spectra by multivariate analysis (SA-MVA) is used to assess risk of bone fracture. Such methods are described for example in Canon et al. (U.S. patent application number 2009/0012403), the content of which is incorporated by reference herein in its entirety. Briefly, a Raman spectrum of a sample of keratinized tissue is generated and broad spectral background features of the spectrum are removed, preferably by using Fourier transform analysis. Peak heights of Raman features of interest, particularly the S—S bond of cystine, are measured. These peak height measurements are normalized using reference peak heights of Raman features that are invariant between normal and osteoporotic subjects, such as the CH$_2$ bending peak.

In another embodiment, FT-IR (Fourier transform-infrared) is used to measure the level of sulfur bonding in a keratinized tissue sample such as nail, hair, or skin, where the keratinized tissue is measured in situ or on a collected keratinized tissue sample. Those skilled in the art recognize that infrared covers a slightly different region of the spectrum than Raman spectroscopy. However methods of configuring the FT-IR apparatus to cover this area of the spectrum are well known in the art.

A number of ways of interpreting spectral data are known in the art and are thus suitable for the diagnostic methods disclosed herein. Thus, for example, spectral data obtained from Raman spectroscopy can be analyzed for differences between control versus test biological samples at any given spectral peak of interest, for example, the peak at 510 cm$^{-1}$ corresponding to disulfide bonds (S—S, gauche-gauchegauche conformation) and the peaks at about 621 cm$^{-1}$ and 643 cm$^{-1}$ corresponding to carbon sulfide bonds (C—S). At any given spectral peak, the difference between a control and test biological sample can be analyzed based upon a comparison of the width at half maximum height of the peak, the relative peak height, area integration (i.e., area under the peak), combinations thereof, and the like. In some embodiments, the diagnostic assays described herein are based on comparisons of the width at half maximum height (WHM) of the Raman spectral peak that corresponds to disulfide bonds of a keratinized tissue such as nail, hair, or skin (i.e., the peak at about 510 cm$^{-1}$). However, it is recognized that any methodology can be utilized to compare differences in the Raman spectra obtained from keratinized tissue samples, for example, differences occurring at the spectral peak appearing at about 510 cm$^{-1}$.

Those skilled in the art recognize that diagnostic assays can be described in terms of accuracy. Accuracy refers to mean the total number of results of a given test divided by the number of incorrect results. Incorrect results are a function of error rates present in the assay and include but are not limited to measurement error, user error, reporting error, and the like. Diagnostic assays can be further described in terms of false positive and false negative rates. False positive and false negative rates are generated by comparing the results of an assay against a gold standard. A gold standard refers to a reference standard that is unlikely to be incorrect or has been traditionally used to define the disease, such as bone mineral density for osteoporosis. False positive and false negative rates affect the sensitivity and specificity of an assay.

The sensitivity of a test is the probability that it will produce a true positive result when used on a diseased population (as compared to a reference or "gold standard"). The sensitivity of a diagnostic test is calculated as: (the number of true positive results)/(the number of true positive results+the number of false negative results). The specificity of a test is the probability that a test will produce a true negative result when used on a non-diseased population (as determined by a reference or "gold standard"). The specificity of a test is calculated as: (the number of true negative results)/(the number of true negative results+the number of false positive results). The sensitivity and specificity of a diagnostic test indicates possible uses within a particular population. For example, high sensitivity tests are useful in screening populations where the disease to be diagnosed is relatively serious and the treatment is relatively inexpensive and readily available because the cost of a failing to detect a diseased patient is high (false negative) and the cost of treating an undiseased patient is low (false positive). Alternatively, high specificity tests are useful in screening populations where the disease is not as serious and the treatment is relatively expensive because the few undiagnosed, diseased patients (false negatives) within the population will not suffer greatly as compared to the unnecessary treatment of many non-diseased patients (false positives). It is routine within the art to adjust the specificity and sensitivity of assays or use variant assays with differing sensitivity and specificity to screen specific populations. The sensitivity of the disclosed methods for the detection of a bone disease such as osteoporosis is at least about 70%, preferably at least about 75%, 80%, 85%, more preferably at least about 90, 91, 92, 93, 94, 95, 96, 97, 98, 99% or more, depending upon the diagnostic method used. Furthermore, the specificity of the present methods for detection is at least about 50%, preferably at least about 60%, 70%, 75%, 80%, more preferably at least about 90, 91, 92, 93, 94, 95, 96, 97, 98, 99% or more, depending upon the diagnostic method used.

Measurements of hardness, modulus, or level of sulfur bonding in a keratinized tissue sample find use in screening any population in need of treatment. Those skilled in the art are routinely able to determine the false negative and false positive rates of these assays. Also, those skilled in the art recognize that statistical measures such as accuracy, specificity, and sensitivity are equally applicable to continuous as well as nominal variables. Thus, the diagnostic methods described herein can be used to assess not only the presence or absence of disease (i.e., nominal variable) but also the extent or severity of disease (i.e., continuous variable).

Those skilled in the art also recognize that results of the individual diagnostic assays disclosed herein can be combined with other assays previously known in the art to further refine the accuracy, specificity, and sensitivity of the diagnosis. Thus, the assays disclosed herein may be used in conjunction with such other diagnostic indicators such as clinical presentation, decrease in bone mineral density, radiographic evidence of osteopenia or vertebral deformity, loss of height, thoracic kyphosis, previous fragility fracture, prolonged corticosteroid therapy, premature menopause, prolonged secondary amenorrhea, primary hypogonadism, chronic disorders associated with osteoporosis (e.g., anorexia nervosa, malabsorption syndromes), maternal history of hip fracture, serum prevalence of C-telopeptide of type I collagen, low calcaneal ultrasonic variables (BUA and SOS), low body mass index, and the like.

Those skilled in the art also recognize that the diagnostic assays described herein may be routinely used for prognostic assays. Specifically, the results of a diagnostic assay (e.g., changes in hardness, modulus, or level of sulfur bonding in a keratinized tissue sample) can be correlated to another variable (or combination of variables) of interest, such as the mean time before death, the recovery rate, the relapse rate, the progression rate, the severity of disease, the treatment response rate, molecular diagnostics, and the like, to predict a clinical outcome. Both historical and contemporaneous data on patients are routinely available. These data may be positively or negatively correlated with changes in hardness, modulus, or level of sulfur bonding of a keratinized tissue sample.

The statistical relationships between the results of the diagnostic assay and a known outcome are useful in generating a correlation coefficient, which indicates the magnitude of a correlation as compared to a random association between variables. See, for example, Zhou et al. (2002) Statistical Methods in Diagnostic Medicine (Wiley, New York), the content of which is incorporated by reference herein in its entirety. Other methods of correlating relationships are known in the art and these methods may all find use in the methods disclosed herein.

In some embodiments, the prognostic assays disclosed herein are used to stratify osteoporosis patients with increased risk of bone fracture. The term "stratify" is intended to mean that a group sharing a common characteristic, such as having osteoporosis, is subdivided into one or more subclasses.

To determine changes in the physical or chemical structure of a keratinized tissue sample and thereby detect (by any method known in the art including but not limited to the assays disclosed and incorporated by reference herein) the presence of bone disease, or stage of bone disease, such as osteoporosis, the signal generated from a test of the physical or chemical structure of a keratinized tissue sample is generally compared to a threshold signal that corresponds to a predetermined cut-off value. In one embodiment, the cut-off value for the detection of a change in hardness, modulus, or level of sulfur bonding in a keratinized tissue sample is the average signal obtained from keratinized tissue samples collected from subjects without bone disease, for example, those without osteoporosis.

Generally, detecting a decrease (relative to a control sample) in the hardness or modulus of a keratinized tissue sample or a decrease in the level of sulfur bonding in a keratinized tissue sample is indicative of a bone disease, or more specifically fragile bones, such as those found in osteoporosis patients. Physicians can use the assays disclosed herein to generate information that can assist in choosing to initiate, change, or increase/decrease therapeutic regimens, as discussed supra. In addition, a physician may use information provided by the assays disclosed herein to confirm or exclude potential diagnoses based on other diagnostic methods including bone mineral density and other diagnostics.

In some embodiments, the keratinized tissue sample is nail, and Raman spectroscopy is utilized to predict the presence or absence of osteoporosis in a subject. In this manner, a Raman spectrum is collected on nails (in situ or nail clippings) of the subject to be tested, and the level of disulfide bonding is detected by analyzing the intensity of the peak at 510 $cm^{-1}$ of the Raman spectrum. As noted above, intensity of this peak can be determined using any method of spectral analysis known in the art. The intensity of this peak represents a bone quality score for the individual and is indicative of the presence or absence of, or risk of developing, osteoporosis. In one embodiment, the intensity of the peak at 510 $cm^{-1}$ of the Raman spectrum for nails is calculated based on the width at half maximum (WHM) value of this peak. A mean WHM value at or above about 35 $cm^{-1}$ is indicative of an individual having a bone mineral density (BMD) T-score of $\leq -1.5$ (as measured by DEXA; see FIG. 5). In accordance with the World Health Organization's definition and categorization of osteoporosis, a BMD T-score of $\leq -1.5$ is indicative of low bone mass, while a BMD T-score of $\leq -2.5$ indicates the presence of osteoporosis. The sensitivity of this diagnostic test to predict a BMD T-score of $\leq -2.5$ (and thus presence of osteoporosis) in a population of 52 women participating in a blind clinical trial was 93.3%, while the specificity of the test to predict this BMD T-score was 95.5% (see Example 2 herein below).

Figure 6:
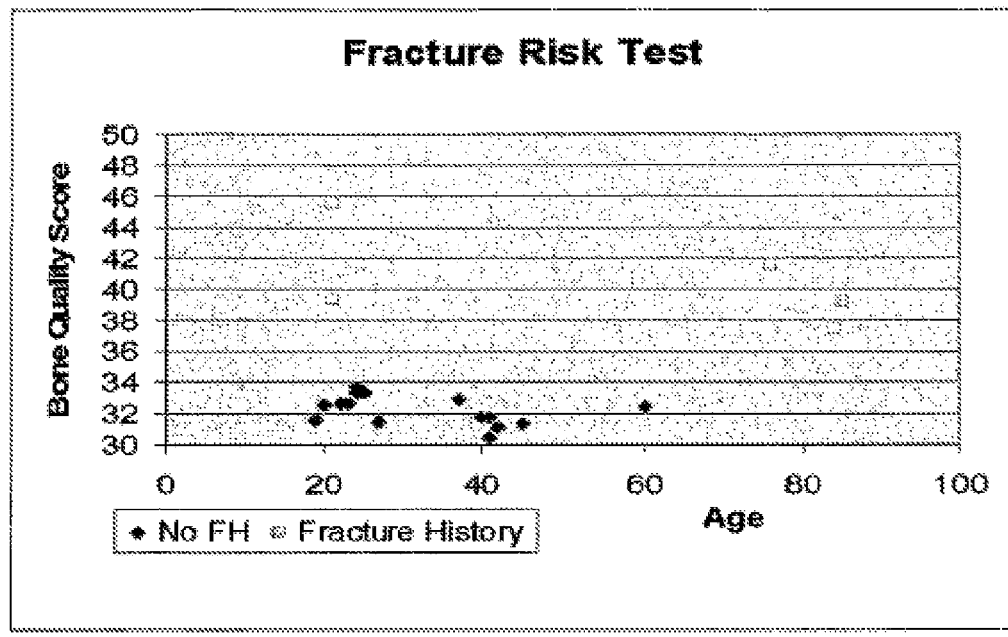
FIG. 6 plots fracture risk history as a function of age and bone quality test score based on WHM for the S—S peak from the Raman spectra for healthy and at risk women.

In other embodiments, a mean WHM value at or above about 35 $cm^{-1}$ for the peak at 510 $cm^{-1}$ of the Raman spectrum for nails is indicative of an individual who is at risk for fracture, for example, fracture associated with a bone disease such as osteoporosis (see FIG. 6). Where an individual tests positive (for example, a mean WHM value at or above about 35 $cm^{-1}$ for the peak at 510 $cm^{-1}$ of the Raman spectrum for nail samples), proactive medical therapy to slow loss of bone mass, disease progression, and to reduce fracture risk can be implemented. One of skill in the art will recognize that subsequent diagnostic assays conducted in a similar manner, e.g., spectral analysis of a keratinized tissue such as nails, for an individual undergoing medical therapy for the bone disease, can provide a means of monitoring treatment efficacy.

Bone-Fracture Risk Factors

In certain embodiments, methods of the invention assess risk of bone fracture by correlating assay results with an analysis of risk factors that may be associated with bone fracture. Exemplary bone fracture risk factors include age, sex, weight, height, previous fracture, parental hip fracture, glucocorticoids, rheumatoid arthritis, body mass index (BMI), smoking status, thyroid hormone use, age at menopause (e.g., greater or less than 45 years old), type I diabetes, stroke, alcohol consumption (greater than or less than 3 units/day), or diagnosis of osteoporosis. Additional bone fracture risk factors are shown in McCloskey et al. (Curr Osteoporos Rep 7:77-83, 2009), the content of which is incorporated by reference herein in its entirety.

Methods including Cox's proportional hazards, logistic regression analysis and chi square tests may be used to identify an association between keratinized tissue and bone fracture risk. In addition, when using logistic regression, adjustments for covariates like age, smoking, BMI and other factors that effect bone risk fracture, such as those discussed above, may be included in the analysis.

The association between keratinized tissue and bone fracture risk may be analyzed within cases only or comparing cases and controls using analysis of variance. Such analysis may include, adjustments for covariates like age, smoking, BMI and other factors that effect bone fracture risk.

Method of logistic regression are described, for example in, Ruczinski (Journal of Computational and Graphical Statistics 12:475-512, 2003); Agresti (An Introduction to Categorical Data Analysis, John Wiley & Sons, Inc., 1996, New York, Chapter 8); and Yeatman et al. (U.S. patent application number 2006/0195269), the content of each of which is hereby incorporated by reference in its entirety.

Other algorithms for analyzing associations are known. For example, the stochastic gradient boosting is used to generate multiple additive regression tree (MART) models to predict a range of outcome probabilities. Each tree is a recursive graph of decisions the possible consequences of which partition patient parameters; each node represents a question (e.g., is the patient a smoker?) and the branch taken from that node represents the decision made (e.g. yes or no). The choice of question corresponding to each node is automated. A MART model is the weighted sum of iteratively produced regression trees. At each iteration, a regression tree is fitted according to a criterion in which the samples more involved in the prediction error are given priority. This tree is added to the existing trees, the prediction error is recalculated, and the cycle continues, leading to a progressive refinement of the prediction. The strengths of this method include analysis of many variables without knowledge of their complex interactions beforehand.

A different approach called the generalized linear model, expresses the outcome as a weighted sum of functions of the predictor variables. The weights are calculated based on least squares or Bayesian methods to minimize the prediction error on the training set. A predictor's weight reveals the effect of changing that predictor, while holding the others constant, on the outcome. In cases where one or more predictors are highly correlated, in a phenomenon known as collinearity, the relative values of their weights are less meaningful; steps must be taken to remove that collinearity, such as by excluding the nearly redundant variables from the model. Thus, when properly interpreted, the weights express the relative importance of the predictors. Less general formulations of the generalized linear model include linear regression, multiple regression, and multifactor logistic regression models, and are highly used in the medical community as clinical predictors.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Physical and Chemical Changes in Human Fingernails as Correlates of Bone Disease The current noninvasive testing methods for osteoporosis use dual energy x-ray absorptiometry (DEXA) scanners or ultrasound-based scans that measure bone density. These tests require expensive diagnostic equipment and trained personnel, thereby limiting their application.

The diagnostic assays described in Example 1 below represent novel noninvasive diagnostic tests for osteoporosis, which for purposes of this invention are referred to as Bone Quality Tests (BQT). BQT measures the chemical properties (microarchitecture) of a keratinized tissue such as the nail as opposed to measuring bone density. The BQT is based on the finding that there is a statistically significant difference in the state of the proteins, particularly keratin, between the nails of a healthy person and those of a person with osteoporosis. Thus, the microarchitecture of the nail can be used as an analogue for bone quality.

The BQT is a much simpler methodology, and is potentially more cost effective, than other forms of noninvasive osteoporosis detection methods available today. The BQT can detect osteoporosis fracture risk noninvasively and inexpensively, and will allow primary care practitioners to proactively manage osteoporosis diagnosis and treatment.

Example 1 below demonstrates two means by which the state of proteins in nails can be determined, i.e., nanoindentation and spectroscopic analysis. The latter can be monitored using any spectroscopic methodology, for example, Raman spectroscopy (as demonstrated below), NIR, and FT-IR, as noted elsewhere herein above. Example 2 describes the results of a blind clinical trial undertaken to verify the specificity and sensitivity of the BQT based on Raman spectral analysis.

Two groups of subjects were identified. The first group (n=9) was diagnosed by DEXA (Lunar Prodigy, GE Medical systems), as osteoporotic (T score<−2.5). The second group (n=13) was diagnosed as non-osteoporotic (T score>1.0). All statistical tests correlating disease to various dependent variables were performed using ANCOVA.

Fingernail clippings were obtained from all subjects. The nail apparatus is composed of the nail fold, nail matrix, nail bed, and the hyponychium, which together form the nail plate. This nail plate is produced mainly by the matrix and emerges via the proximal nail fold, while being held in place by the lateral nail fold. It overlays the nail bed and detaches at the point called the hyponychium, or where the free edge of the plate ends. This is where the clipping is taken (see FIG. 1). This area corresponds to the area where high-sulfur keratin, typical of hard keratins, is found. Following their sourcing, samples were stored in sealed specimen jars prior to testing.

Notably, the physical properties of fingernails change when soaked in water, as it becomes soft and flexible. It is thought that the degree of hydration is the most important factor influencing the physical properties of nails because chemically bound water is found in both dry and wet nails. The water-protein interaction changes the keratin structure giving it new mechanical characteristics (Finlay et al. (1980) Br J Dermatol. 103:357; and Wessel et al. (1999) Biochim Biophys Acta. 1433:210). This highlights the need to store nail-clipping samples under conditions where they are not exposed to large amounts of water or dehydrated prior to testing. Accordingly, the nails were stored in sealed jars not more than one month before testing.

Experiments performed on nails stored over time confirmed that nails stored in the manner disclosed above maintained the same properties over at least a one month period. Specifically, nail samples were tested weekly over a period of one month for hardness and modulus to confirm that no detectable changes had occurred. In contrast, nail samples that were tested one year after collection exhibited different properties.

Nanoindentation

The nails were trimmed prior to testing to expose the flat mid-section of each nail, and, therefore, reduce the possibility of the curved edges of the nail making premature contact with the indenter. Samples were then attached to aluminium stubs with an epoxy adhesive (part no: 46409, Versachem, FL, USA).

Nanoindentation experiments were conducted using a laboratory-built machine previously described by Arteaga et al. (1993) Tribology Int'l. 26:305. For each indentation, the tip was brought into contact with the surface using a load of a few .mu.N. The load was then increased linearly at 0.8 mNs-.sup.-1 up to its maximum value of 120 mN, and then reduced again at the same rate to zero. Every 150 ms during the cycle readings were taken of the displacement of the indenter .delta., and the load P, allowing the examination of force-penetration data during both the loading and unloading phases. Consequently, it is possible to produce curves of penetration depth at each force level during the loading and unloading phases. The data for these studies were generated using the Formulae 1-3, supra. A schematic representation of a nanoindentation curve is given in FIG. 2. The collected data are shown in Table 1, and the statistical analysis is shown in Table 2.

TABLE 1

Measurements of modulus and harness of fingernail clippings.

| Sample | Modulus | Max. Hardness | Min. Hardness | BMD |
|---|---|---|---|---|
| A(1) | 3.43 | 0.247 | 0.236 | 2 |
| A(2) | 3.09 | 0.186 | 0.164 | 2 |
| A(3) | 3.88 | 0.386 | 0.325 | 2 |
| A(4) | 3.38 | 0.23 | 0.201 | 2 |
| A(5) | 3.47 | 0.298 | 0.256 | 2 |
| G2(1) | 3.25 | 0.201 | 0.173 | 2 |
| G2(2) | 3.14 | 0.202 | 0.175 | 2 |
| G2(3) | 3.79 | 0.193 | 0.171 | 2 |
| G2(4) | 3.64 | 0.15 | 0.132 | 2 |
| G2(5) | 3.17 | 0.194 | 0.172 | 2 |
| H2(1) | 2.95 | 0.266 | 0.234 | 2 |
| H2(2) | 4.51 | 0.497 | 0.424 | 2 |
| H2(3) | 4.11 | 0.415 | 0.352 | 2 |
| H2(4) | 6.24 | 0.614 | 0.522 | 2 |
| H2(5) | 3.62 | 0.219 | 0.189 | 2 |
| D(1) | 3.5 | 0.0693 | 0.0645 | 0 |
| D(2) | 3.34 | 0.0626 | 0.0565 | 0 |
| D(3) | 3.26 | 0.0578 | 0.0522 | 0 |
| D(4) | 2.71 | 0.0407 | 0.0369 | 0 |
| E(1) | 4.34 | 0.299 | 0.268 | 0 |
| E(2) | 5.1 | 0.41 | 0.353 | 0 |
| E(3) | 4.62 | 0.36 | 0.31 | 0 |
| E(4) | 4.86 | 0.388 | 0.337 | 0 |
| E(5) | 4.86 | 0.388 | 0.337 | 0 |
| F(1) | 3.51 | 0.273 | 0.237 | 0 |
| F(2) | 3.33 | 0.293 | 0.253 | 0 |
| F(3) | 3.17 | 0.134 | 0.117 | 0 |

TABLE 1-continued

Measurements of modulus and harness of fingernail clippings.

| Sample | Modulus | Max. Hardness | Min. Hardness | BMD |
|---|---|---|---|---|
| G(1) | 5.12 | 0.212 | 0.187 | 0 |
| G(2) | 5.27 | 0.345 | 0.3 | 0 |
| G(3) | 4.57 | 0.243 | 0.219 | 0 |
| G(4) | 5.27 | 0.275 | 0.239 | 0 |
| G(5) | 5.79 | 0.351 | 0.302 | 0 |
| H(1) | 4.83 | 0.394 | 0.329 | 0 |
| H(2) | 4.12 | 0.261 | 0.226 | 0 |
| H(3) | 4.36 | 0.265 | 0.224 | 0 |
| H(4) | 4.69 | 0.293 | 0.259 | 0 |
| H(5) | 5.4 | 0.359 | 0.298 | 0 |
| I(1) | 2.47 | 0.12 | 0.109 | 0 |
| I(2) | 2.93 | 0.0536 | 0.0506 | 0 |
| I(3) | 3.03 | 0.0756 | 0.0698 | 0 |
| I(4) | 2.8 | 0.135 | 0.122 | 0 |
| I(5) | 3.15 | 0.154 | 0.141 | 0 |
| J(1) | 3.08 | 0.101 | 0.0885 | 0 |
| J(2) | 3.4 | 0.0762 | 0.0706 | 0 |
| J(3) | 2.82 | 0.0609 | 0.056 | 0 |
| J(4) | 2.64 | 0.0782 | 0.0714 | 0 |
| J(5) | 3.83 | 0.125 | 0.112 | 0 |
| K(1) | 4.95 | 0.342 | 0.295 | 0 |
| K(2) | 6.42 | 0.485 | 0.416 | 0 |
| K(3) | 5.48 | 0.415 | 0.356 | 0 |
| K(4) | 6.36 | 0.61 | 0.51 | 0 |
| K(5) | 7.24 | 0.565 | 0.491 | 0 |
| L(1) | 3.45 | 0.309 | 0.263 | 0 |
| L(2) | 3.5 | 0.233 | 0.204 | 0 |
| L(3) | 4.42 | 0.447 | 0.376 | 0 |
| L(4) | 3.94 | 0.31 | 0.27 | −3 |
| N(1) | 0.967 | 0.279 | 0.236 | −3 |
| N(2) | 1.27 | 0.275 | 0.237 | −3 |
| N(3) | 0.933 | 0.145 | 0.131 | −3 |
| N(4) | 1.49 | 0.297 | 0.255 | −3 |
| N(5) | 1.49 | 0.236 | 0.207 | −3 |
| O(1) | 3.86 | 0.179 | 0.158 | −3 |
| O(2) | 2.88 | 0.124 | 0.112 | −3 |
| O(3) | 2.53 | 0.073 | 0.0663 | −3 |
| O(4) | 2.84 | 0.0987 | 0.0903 | −3 |
| O(5) | 2.82 | 0.072 | 0.0672 | −3 |
| P(1) | 1.83 | 0.121 | 0.103 | −3 |
| P(2) | 1.63 | 0.148 | 0.128 | −3 |
| P(3) | 2.67 | 0.0898 | 0.0814 | −3 |
| P(4) | 0.856 | 0.0503 | 0.0472 | −3 |
| Q(1) | 1.41 | 0.0425 | 0.0405 | −3 |
| Q(2) | 1.68 | 0.0768 | 0.0726 | −3 |
| Q(3) | 1.49 | 0.133 | 0.121 | −3 |
| Q(4) | 1.74 | 0.165 | 0.148 | −3 |
| Q(5) | 1.97 | 0.183 | 0.161 | −3 |
| R(2) | 5.06 | 0.376 | 0.324 | −3 |
| R(3) | 5.6 | 0.52 | 0.439 | −3 |
| R(4) | 4.61 | 0.305 | 0.261 | −3 |
| R(5) | 6.12 | 0.638 | 0.52 | −3 |
| S(1) | 3.02 | 0.0996 | 0.0908 | −3 |
| S(2) | 4.47 | 0.37 | 0.324 | −3 |
| S(3) | 3.58 | 0.21 | 0.185 | −3 |
| S(4) | 3.61 | 0.18 | 0.155 | −3 |
| S(5) | 3.81 | 0.31 | 0.263 | −3 |
| T(1) | 3.68 | 0.198 | 0.179 | −3 |
| T(2) | 3.58 | 0.137 | 0.125 | −3 |
| T(3) | 4.01 | 0.295 | 0.251 | −3 |
| T(4) | 2.99 | 0.148 | 0.134 | −3 |
| T(5) | 3.3 | 0.105 | 0.0978 | −3 |
| U(1) | 2.27 | 0.172 | 0.153 | −3 |
| U(2) | 1.21 | 0.122 | 0.114 | −3 |
| U(3) | 3.56 | 0.263 | 0.233 | −3 |
| U(4) | 4.08 | 0.299 | 0.262 | −3 |
| U(5) | 3.2 | 0.138 | 0.126 | −3 |
| V(1) | 4.08 | 0.144 | 0.133 | −3 |
| V(2) | 4.39 | 0.131 | 0.116 | −3 |
| V(3) | 6.23 | 0.458 | 0.398 | −3 |
| V(4) | 4.33 | 0.142 | 0.134 | −3 |
| V(5) | 3.75 | 0.277 | 0.242 | −3 |

TABLE 2

Statistical analysis of collected data

High BMD Group

| | | | |
|---|---|---|---|
| mean modulus | 3.711333333 | mean hardness | 0.267467 |
| standard deviation | 0.81434344 | standard deviation | 0.121951 |

Normal BMD Group

| | | | |
|---|---|---|---|
| mean modulus | 4.193414634 | mean hardness | 0.238365 |
| standard deviation | 1.162156637 | standard deviation | 0.139288 |

Low BMD Group

| | | | |
|---|---|---|---|
| mean modulus | 3.044093023 | mean hardness | 0.192416 |
| standard deviation | 1.413736299 | standard deviation | 0.117027 |

All Non-Osteoporotic

| | | | |
|---|---|---|---|
| mean modulus | 4.064285714 | mean hardness | 0.24616 |
| standard deviation | 1.094289071 | standard deviation | 0.134947 |

Mean elastic moduli and hardness results for the two sets of fingernails are included below in Table 3.

TABLE 3

Mean moduli and hardness (and standard deviations) of fingernails sourced

| Subject Group | Moduli (GPa) | Hardness (GPa) |
|---|---|---|
| Osteoporotic | 3.0 (±1.5) | 0.19 (±0.12) |
| Healthy | 4.1 (±1.1) | 0.23 (±0.14) |

The mean moduli of fingernails from patients with low BMD are approximately 25% lower than those with normal BMD. The difference in mean modulus between the groups was found to be 1.1 GPa, which only approached significance at 5% level (p=0.147) due to a lack of power (small n) within the test.

Raman Spectroscopy

For Raman analysis, four fingernail samples from each group were analyzed to ascertain if there was disparity between groups, and to detect osteoporotic-induced changes in keratinized tissue. Micro Raman spectra were obtained using a Dilor Labram 01 instrument. Excitation was by red laser operating at 632.81 nm. Spectra were obtained by performing 20 scans, to improve the signal-to-noise ratio, each with a laser exposure time of 50 seconds. The same operating procedure was repeated for all samples in order for the resultant spectra to show only the differences between the osteoporotic and non-osteoporotic tissue. Spectra were recorded from 300 $cm^{-1}$ to 1800 $cm^{-1}$ for identification of all the characteristic peaks in human nail. The interval from 300 $cm^{-1}$ to 700 $cm^{-1}$ was selected for comparison. Normalization of all acquired spectra was carried out to facilitate the comparison and to highlight differences between groups.

Figure 3:
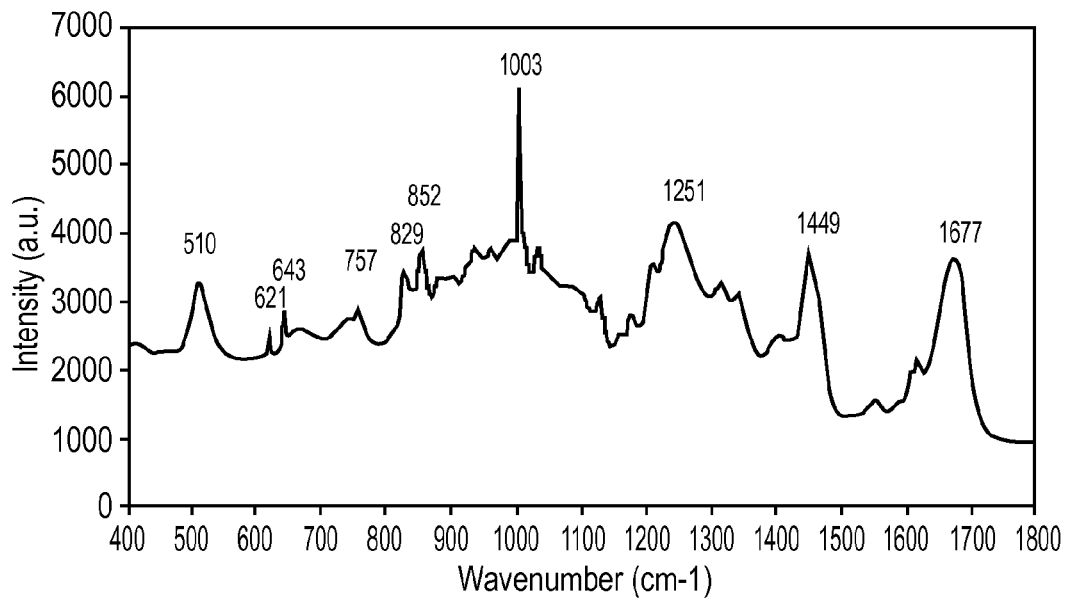
FIG. 3 shows a typical Raman spectrum of the human nail from 300 $cm^{-1}$-1800 $cm^{-1}$.

FIG. 3 shows the typical Raman spectrum of human nail between 300 $cm^{-1}$ and 1800 $cm^{-1}$. The major spectral peaks of human nail include the amide band at 1677 $cm^{-1}$ indicating that nail keratin is predominantly .alpha.-helical, the methylene ($CH_2$) deformation band at 1450 $cm^{-1}$ and the amide [v(CN)] band at 1251 $cm^{-1}$. In the 1000 $cm^{-1}$ to 1200 $cm^{-1}$ region the strongest band occurs at 1006 $cm^{-1}$, corresponding to the C—C stretching vibration of the aromatic ring in the phenylalanine side chain. However, it is the lower region of the spectrum that is of most concern in this study. The area between 700 $cm^{-1}$ and 300 $cm^{-1}$ contains the spectral information about the sulfur bonding in fingernails. The relative intensities of the S—S and C—S stretching vibrations give a good indication of the amount of sulfur present and allow determination of the structural configuration of the S—S bond. FIG. 3 shows the peak at 510 cm$^{-1}$ representing the disulfide bonding [ν(SS)]. Lesser peaks at 621 cm$^{-1}$ and 645 cm$^{-1}$ represent carbon sulfide bonding [ν(CS)].

Figure 4:
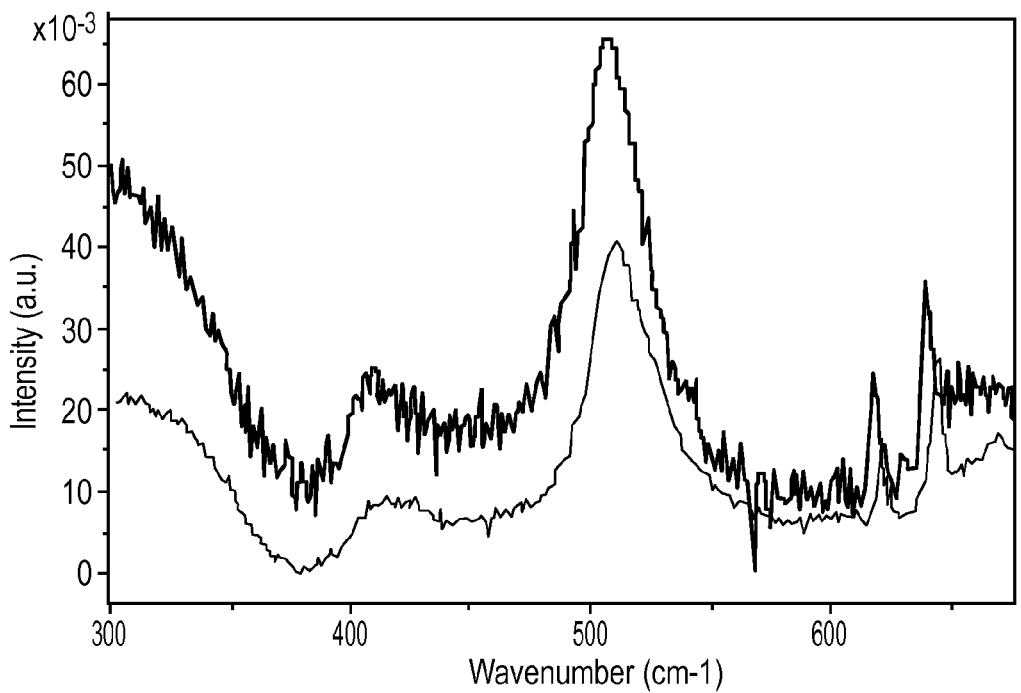
FIG. 4 shows two Raman spectra, one from a non-osteoporotic (healthy) individual (top) and one from an osteoporotic individual (bottom).

FIG. 4 shows normalized Raman spectra for an osteoporotic and non-osteoporotic nail on the same scale. Two main differences between osteoporotic and normal nails were observed. The disulfide bond (S—S, gauche-gauche-gauche conformation) peak for healthy nail at 510 cm$^{-1}$ was much sharper than for the osteoporotic nail and the width of the S—S peak in osteoporotic nail was found to be larger than the healthy nail. Therefore, the disulfide bond content of the nails sourced from osteoporotic patients was lower than those from healthy patients. Table 4 shows that this difference in mean width at half maxima for the S—S peak from the two sets of nails is statistically significant (ANCOVA).

TABLE 4

Raman spectroscopy results for osteoporotic versus non-osteoporotic nail

| Width at half maxima for the S-S peak | (cm$^{-1}$) Minimum | (cm$^{-1}$) Maximum | (cm$^{-1}$) Mean | Std. Deviation |
|---|---|---|---|---|
| Non-osteoporotic | 25.00 | 30.70 | 27.68 | 2.39 |
| Osteoporotic | 37.50 | 42.30 | 39.20 | 2.12 |

There was also a shift in the carbon sulfide bond (C—S) peak at about 621 cm$^{-1}$ and 643 cm$^{-1}$ as shown by the higher wave numbers detected for the C—S bonds in osteoporotic nail.

In protein spectra the C—S vibrational band originates from methionine, cysteine and cystine. Since methionine content in human nail is negligible, the C—S and S—S bands shown must have originated from cysteine and cystine (Marshall et al. (1996) BMJ 312:1254). While not being bound by any particular mechanism or theory of action, the shift in the carbon sulfide bonding may be due to the change of the sulfur content in the nails since it is known that the C—S stretching vibration is dependent on the conformation of its side chains.

Example 2

Verification of Bone Quality Test Based on Raman Spectral Analysis of Nails

The World Health Organization (WHO) defines osteoporosis as "a skeletal disorder characterized by compromised bone strength predisposing a person to an increased risk of fracture." The WHO uses the bone mineral density (BMD) T-score as the standard for identifying the osteoporotic condition. To obtain the T-score, an individual's BMD result (for example, from DEXA) is compared with the BMD results from healthy 25- to 35-year-old adults of the same sex and ethnicity. The standard deviation (SD) is the difference between your BMD and that of the healthy young adults. This result is the "T-score." Positive T-score values are indicative of bone that is stronger than normal; negative T-score values are indicative of bone that is weaker than normal. According to the WHO, osteoporosis is categorized based on the following bone mineral density levels:

A T-score within 1 SD (+1 or −1) of the young adult mean indicates normal bone density;

A T-score of 1 to 2.4 SD below the young adult mean (−1 to −2.5 SD) indicates low bone mass;

A T-score of 2.5 SD or more below the young adult mean (greater than −2.5 SD) indicates the presence of osteoporosis.

In general, the risk for bone fracture doubles with every SD below normal. Thus, for example, a person with a T-score of −1 has twice the risk for bone fracture as a person with a normal BMD. A person with a T-score of −2 has four times the risk for bone fracture as a person with a normal BMD. When this information is known, people with a high risk for bone fracture can be treated with the goal of preventing future fractures.

The present example provides the results of a blind clinical trial that was carried out to identify women, based on the BQT, who were defined as having osteoporosis using the World Health Organization (WHO) definition for this condition (i.e., a BMD T-score of less than (i.e., more negative than) or equal to −2.5 (e.g., −3.0). The sample size was 52 patients, and the BQT data were obtained using Raman spectroscopy of fingernail samples collected from these patients, and analyzing for differences in the Raman spectral peak at 510 cm$^{-1}$ (i.e., the S—S peak).

Figure 5:
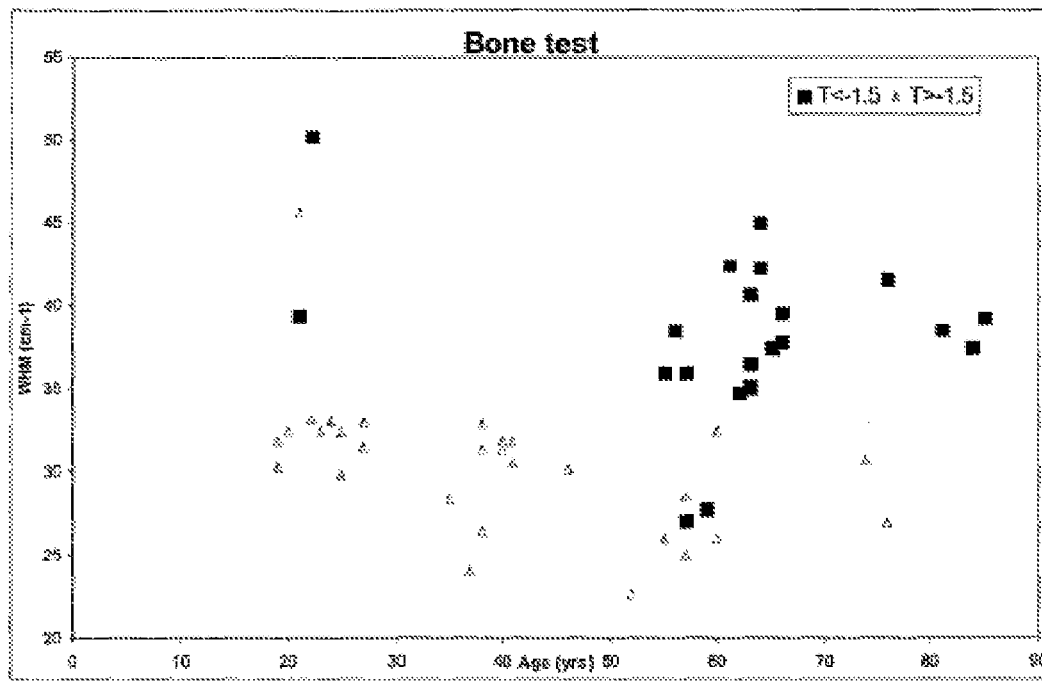
FIG. 5 plots T-score as a function of age and bone quality test score based on the width at half maxima (WHM) for the S—S peak from the Raman spectra for patients in the blind clinical trial referred to in Example 2.

In this manner, fingernail clippings from these subjects were examined using Raman spectroscopy (spectra obtained with a Dilor Labram 01 instrument) in a manner similar to that described in Example 1. For this study, the width at half maxima (WHM) for the S—S peak from the Raman spectrum was determined for nails collected from each individual, and the relationships between T-score and age and T-score and WHM value in order to evaluate T-score as a function of WHM and age. Results are shown in FIG. 5. Table 5 shows the number of non-osteoporotic and osteoporotic patients that had a high WHM value (i.e., 35 cm$^{-1}$ or greater) and low WHM value (i.e., about 34 cm$^{-1}$ or less).

TABLE 5

Distribution of non-osteoporotic and osteoporotic patients based on WHM value obtained from BQT using Raman spectral analysis of nails.

|  | Non-Osteoporotic | Osteoporotic |
|---|---|---|
| WHM High | 1 | 28 |
| WHM Low | 21 | 2 |

Sensitivity of the BQT (i.e., the proportion of patients who tested positive and have osteoporosis) was 93.3% (i.e., 28/30). Specificity of the BQT (i.e., the proportion of patients who tested negative and do not have osteoporosis) was 95.5% (i.e., 21/22). Table 6 shows the comparative sensitivity and specificity of the BQT and other diagnostic tests to predict osteoporosis (i.e., a T-score ≤ −2.5).

TABLE 6

Comparison of BQT with other diagnostic tests to predict T score ≤ −2.5

| Test Method | Sensitivity | Specificity |
|---|---|---|
| BQT | 93.3% | 95.5% |
| QUS | 88%-100% | 47% |
| pDXA | 94% | 69% |
| SCORE | 65.7% | 61.1% |
| Questionnaire | 93.3% | 46.4% |

For information regarding the use of these other diagnostic tests as predictors of osteoporosis, see, for example, Naganathan et al. (1999) Med. J. Aust. 171:297-300 (quantative heel ultrasound (QUS)); Ross and Simon (1998) J. Bone Miner. Res. 23(suppl):S601, Rea et al. (2000) Osteoporos Int. 11(8):660-8, and Rea et al. (2000) J. Bone Miner. Res. 15(3):

564-74 (pDXA); Orthopaedic Nursing 24(1):33-39 (SCORE), and Cadarette et al. (2000) C.M.A.J. 162(9):1289-94 (Questionnaire).

These results indicate that a positive result on the BQT is equivalent to a DEXA T-score of −2.5 or less, and treatment should be considered accordingly.

In another assessment of the predictive value of the BQT, the fracture risk as a function of the bone quality score and age was determined for a subset of the women participating in this trial. As can be seen from FIG. 6, women with fracture histories have very different bone quality scores (WHM score value over about 36 cm$^{-1}$) from women with no fracture history (WHM score value below about 34 cm$^{-1}$).

Thus Raman spectroscopy of nails, either in situ or as nail clippings, can assess fracture risk in a more rapid and less expensive manner that avoids potential problems associated with radiation assessment. Further, a desktop Raman spectroscopy apparatus such as that described in Example 3 below, could be made readily available to practitioners to support mass screening of subjects for the presence or absence of a disease such as osteoporosis, to follow treatment efficacy of individuals having or at risk of developing a bone disease such as osteoporosis, and to predict fracture risk. A reduction in fractures based on more screening and preventative treatment could have significant health and economic benefits worldwide and expand the osteoporosis preventative drug market considerably.

Example 3

Raman Spectroscopy Apparatus for Assessing Osteoporosis and Fracture Risk

Figure 7:
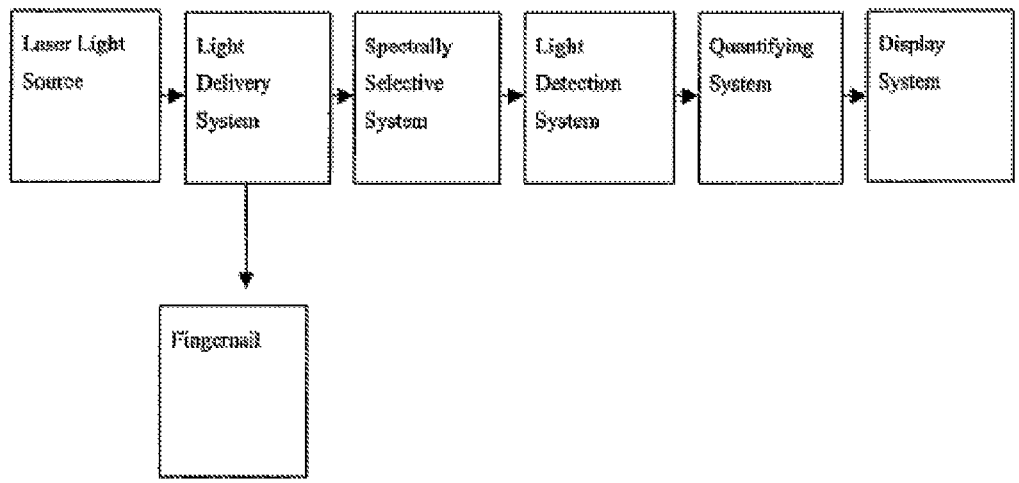
FIG. 7 outlines the components of a Raman spectroscopy apparatus for use in obtaining Raman spectra from keratinized tissue samples such as nails either in situ or as nail clippings for a subject undergoing testing for a bone disease such as osteoporosis.

Any commercially available Raman spectroscopy system can be utilized in the diagnostic assays described herein. FIG. 7 illustrates the main components that can be found within such a system for use in conducting Raman spectral analysis of a keratinized tissue such as nail, either in situ or as nail clippings. The components can be assembled as part of an individual package, or can be constructed as multiple units that are integrated for operation and spectral analysis. In order to collect the spectral data, a probe is placed against the nail of a subject, for example, an intact fingernail of a finger, and a beam of light from the light source is delivered to the nail surface, for example, by pressing a button on the apparatus. The light delivery time can vary, but can be as short as 2-5 seconds. Following spectral selection for Raman scattered light, detection of the Raman scattered light, and quantification, the spectral result is displayed, for example, on a screen, and can then be written to a chip with a data stamp.

Example 4

Combining Analytical Measurements with Other Clinical Risk Factors

A nested case control study design was used within the Nurses' Health Study cohort. Archived nail samples from women 58 to 63 y were analyzed using Raman spectroscopy for 82 women with a hip fracture up to 20 years after nail collection and 81 age-matched controls. A prediction model was developed using multivariate statistical techniques and cross-validated using leave-one-subject-out analysis.

A statistically significant odds ratio of hip fracture per 1 SD change in assay score of 1.60 (1.15-2.22) was found within the women on whom the prediction model was based. Adjusting the model for clinical risk factors increased the odds ratio to 1.84 (95% CI 1.27-2.65).

The data below shows that methods of the invention provide a significant predictor of hip fracture and in combination with clinical risk factors provide superior prediction to risk factors alone.

Nurses' Health Study

The Nurses' Health Study (NHS) is a cohort study involving 121,700 women which commenced in 1976. When the study began, the participants were registered nurses aged between 30 yr and 55 yr living in one of 11 US states. Approximately 96% of the participants are Caucasian. The women have been followed up by questionnaire every two years. Data collected on the biennial questionnaires that are relevant to this investigation include smoking status, weight and height (from which body mass index, BMI, was calculated), thyroid hormone use, stroke, rheumatoid arthritis, type I diabetes, osteoporosis diagnosed by a physician, age at menopause, and use of postmenopausal hormones. Frequency of alcohol consumption was assessed every four years as part of a larger dietary questionnaire.

With respect to hip fracture outcomes, the women were asked to report all previous fractures in 1982 and subsequent fractures were recorded on later questionnaires. Report of hip fracture was expected to be accurate in a population of trained nurses. Validity was examined in a 1986 study that confirmed in thirty reports of hip fracture that all were present in the medical records.

Archived Toenail Clippings

Toenail clippings were collected from 62,865 participants in the NHS cohort between December 1982 and July 1984. Participants were asked to send clippings from all ten toenails. The nail clippings have been stored in a dry environment since collection. The toenail samples used in these investigations were destroyed in processing, therefore 51,430 samples remained in storage.

Study Population and Design

A nested case-control design was selected to establish the ability of methods of the invention to differentiate between women with a history of hip fracture and control subjects. The study population from which the sample was drawn consisted of the women who, at the time of their toenail return, were postmenopausal, 50-63 y, not currently using postmenopausal hormones, and without a hip fracture, stroke, or cancer history (n=13,312). From this population, 279 cases were identified who had a hip fracture from 3 to 20 years after toenail return (median 14.5 years). Hip fractures due to traumatic events (e.g., motor vehicle accident, skiing, horseback riding) were excluded. Of the remaining 13,033 women in the study population who did not report a hip fracture through 2004, one control per case matched on month and year of birth was randomly selected. 82 case-control pairs from the available 279 pairs were randomly selected.

Nail Spectral Measurement

Raman spectral analysis of the toenail samples was conducted without blinding as to case or control status. A Skin Composition Analyzer Model 3510 (River Diagnostics, Rotterdam, NL), using 785 nm laser light of 60±5 mW (at the sample location) with a spectral range of 300-2200 cm$^{-1}$ and spectral resolution 4-5 cm$^{-1}$, was used for measurement. The stability of the Skin Analyzer was checked multiple times a day by polymethylmethacrylate (PMMA) measurements that were compared to a master PMMA spectrum. A correlation of 0.999 was set as the minimum. In order to account for the heterogeneity of the nail, multiple spectra were taken at 2-6 different locations on the nail. The reliability of the resulting average nail spectrum was determined using bootstrapping (Efron, Biometrika 68:589-589, 1981). For each nail, spectral sampling was continued until the confidence interval around the bootstrap mean was smaller than 1.5% of the mean. All nail samples were sufficient for a Raman analysis to be conducted. A spectroscopy reading was not determined for one control subject due to the loss of the toenail samples in transit to the testing lab.

Spectral Processing and Model Development

An EMSC-scaling procedure (Extended Multiplicative Signal Correction) was used to remove the influence of slowly varying backgrounds and the known interfering signal from the sample carrier and to scale the spectra to equal Raman content (Martens et al. Anal Chem 75:394-404, 2003). The EMSC-procedure used a linear fitting model to estimate the contribution of polynomial backgrounds and known interfering signals, and subsequently scale the spectra in such a way that the contributions of both the background and interfering signals were equal in all spectra and that the Raman content in all spectra were comparable in size.

Principal Component Analysis (PCA) and Linear Discrimination Analysis (LDA) was used to develop a predictive multivariate statistical model (Tabachnick B, Fidell L (1996) Using Multivariate Statistics. HarperCollins). The EMSC-scaled Raman spectra were used to identify the key Principal Components (PCs) of variation across the full spectrum range, representing peak shifts and peak shape alterations. The significance of each PC in discriminating between the two predefined groups, hip fractures and controls, was then determined using a t-test. Finally, a LDA model that best discriminated between the fracture and the control group was developed, using only the two most significant PCs to reduce the risk of overfitting the LDA model. The scores of the spectra on the LDA discriminant were used to calculate the probability of belonging to the fracture group.

A leave one subject out (LOSO) cross-validation was performed to validate the prediction model internally. For each subject, a model was developed as described above, using all spectra except the spectra from that subject. Subsequently, the average spectrum of that subject was projected on the multivariate statistical model to yield the probability for that subject belonging to the fracture group. These probability values were used in the subsequent statistical analysis. The scientific computing program Matlab (R2007b) was used to develop all signal processing and multivariate modeling algorithms and scores were generated in a range between 0.0 and 1.0.

Risk of Hip Fracture

The potential of the assay scores to predict hip fracture was examined within the same case/control samples. Odds ratios (ORs) for hip fracture were calculated using both a conditional regression analysis and an unconditional analysis adjusted for age at toenail collection (matching factor for cases and controls). Results from these analyses were very similar and therefore the unconditional model was selected. The assay variable was modeled two ways: per 1 SD change in score and as a positive or negative diagnosis of osteoporosis, using a cut-off (0.50) half way between the extreme scores.

The clinical risk factors included in the algorithms were age, BMI, smoking status, thyroid hormone use, age at menopause (<45 y>), alcohol consumption (<3 units/day>) and diagnosis of osteoporosis.

The assay was further evaluated, excluding the women with a diagnosis of osteoporosis at time of nail collection (2 cases, 4 controls) since these women would not likely be among the candidates for testing. From this subgroup, stratified analyses by age at toenail collection and by years between toenail collection and hip fracture was performed.

Statistical significance was based on two-sided tests with a significance level of p<0.05. A paired t-test was used to determine significant differences between characteristics of the hip fracture cases and their matched controls. Area under the curve (AUC) values were calculated using Receiver Operating Characteristic (ROC) curves. All statistical analyses were carried out using SAS release 9.1.

Characteristics of the Hip Fracture Cases and Controls

Characteristics of the 82 hip fracture case-control pairs at the time of toenail collection are shown in Table 7. Ninety-nine percent of both cases and controls were Caucasian, with one Black subject among the cases and one Asian subject among the controls. As cases and controls were matched on month and year of birth, the mean age (58 y) was identical in both groups. Thyroid hormone use was more prevalent in cases than controls (p=0.02), however all other characteristics were not significantly different between the cases and controls.

TABLE 7

Clinical risk factors at time of toenail collection in hip fracture cases and controls among postmenopausal women in the Nurses' Health Study

|  | Cases (n = 82) | Controls (n = 81) |
| --- | --- | --- |
| Age[a], y (mean) | 57.6 | 57.6 |
| BMI, kg/m$^2$ (mean) | 24.4 | 25.5 |
| Current Smoker (n) | 28 | 21 |
| Osteoporosis (n) | 2 | 4 |
| Rheumatoid Arthritis (n) | 0 | 0 |
| Type I Diabetes (n) | 1 | 0 |
| Age at Menopause < 45 y[b] (n) | 8 | 8 |
| Thyroid Hormone User (n) | 16 | 5 |
| ≥3 Alcoholic Drinks/day (n) | 1 | 3 |

Figure 8:
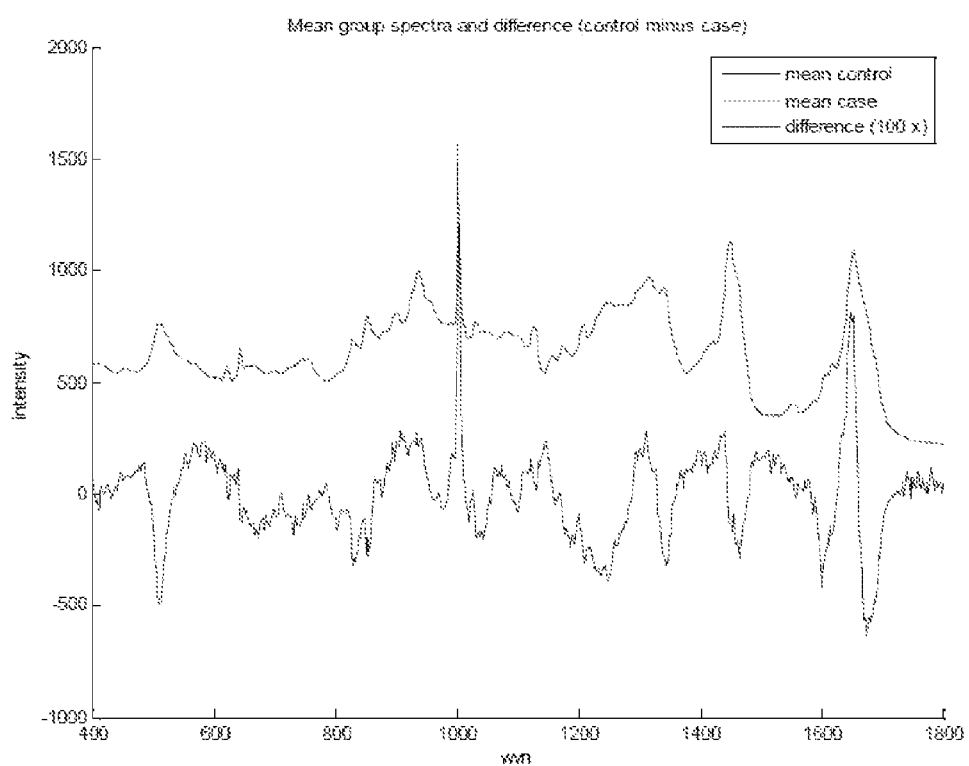
FIG. 8 is a graph showing mean case and control spectra and the difference between cases and controls.

[a] controls were matched to cases on month and year of birth
[b] early age at menopause was due to surgery in 2 of the cases and 3 of the controls Spectral Analysis and Algorithm Model FIG. 8 illustrates the mean spectra grouped into case and control groups. The case and control lines overlap to the naked eye because the differences are too small to be observed without magnification. The mean spectra differences are however reliably detectable using the equipment selected and they are magnified 100 times for illustration in the figure. The ratio of inter group coefficient of variation (CV) to inter-subject CV was greater than 2.0 in the Raman spectra collected.

Prediction Model Results

Figure 9:
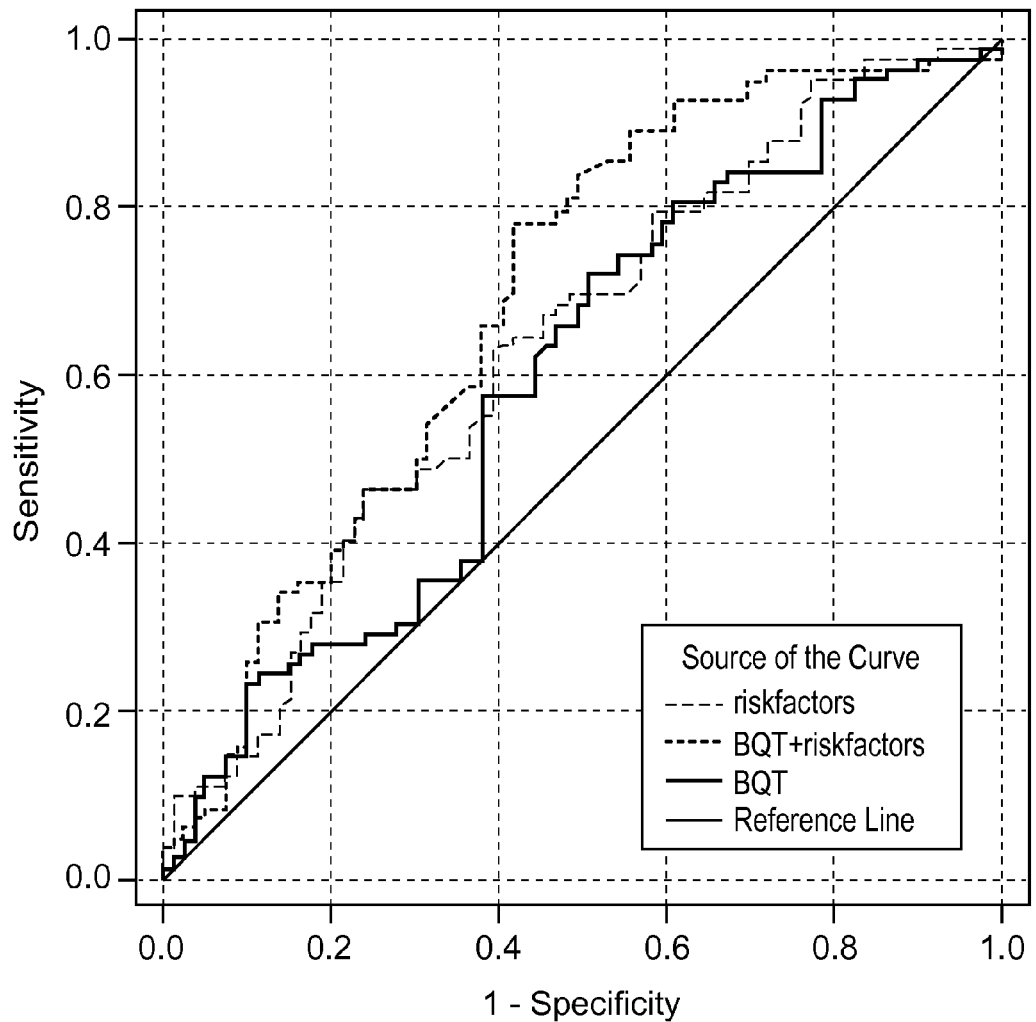
FIG. 9 is a graph showing areas under receiver operator characteristic curve for prediction models for all 82 hip fracture cases and 81 controls.

The average assay score was significantly higher in cases than controls (0.59 vs. 0.51; p=0.004) and receiver operator characteristic (ROC) analysis showed the prediction model to be a significant predictor of future hip fracture (p<0.01) with an area under the curve (AUC) of 0.61; 0.55-0.70) FIG. 9).

The odds ratio (OR) of hip fracture by assay score is shown in Table 8 and the accompanying area under the curve AUC for each model is illustrated in FIG. 9. In the basic model adjusted only for age at toenail collection, the OR was 1.60 (95% CI 1.15-2.22) per 1 SD increase in assay score and an AUC of 0.61. Adjusting the model for the clinical risk factors (age, BMI, smoking status, thyroid hormone use, age at menopause (<45 y>), alcohol consumption (<3 units/day>) and diagnosis of osteoporosis) increased the OR to 1.84 (95% CI 1.27-2.65) with an AUC of 0.69. A model based only on the clinical risk factors had an OR of 2.06 (95% CI 1.4-3.03) and an AUC of 0.63. A statistically significant difference was observed between the ORs for clinical risk factors alone and clinical risk factors in combination with BQT (p=0.001).

TABLE 8

Odds ratio of hip fracture by Bone Quality Test (BQT ®) score from archived toenails among postmenopausal women in the Nurses' Health Study

|  | cases/controls | Basic Model[a] OR (95% CI) |
|---|---|---|
| per 1 SD increase in BQT ®[b] | | |
| total sample | 82/81 | 1.59 (1.15-2.21) |
| exclude prevalent osteoporosis | 80/77 | 1.70 (1.21-2.39) |
| age at nail collection < 58 y | 33/33 | 1.57 (0.93-2.64) |
| age at nail collection ≥ 58 y | 47/44 | 1.82 (1.15-2.86) |
| time to hip fracture < 15 y[c] | 43/40 | 2.01 (1.20-3.35) |
| time to hip fracture ≥ 15 y[c] | 37/37 | 1.47 (0.92-2.35) |
| BQT ® > 0.5 versus ≤ 0.5 | | |
| total sample | 82/81 | 2.50 (1.31-4.79) |
| exclude prevalent osteoporosis | 80/77 | 2.85 (1.47-5.54) |
| age at nail collection < 58 y | 33/33 | 2.83 (1.01-7.90) |
| age at nail collection ≥ 58 y | 47/44 | 2.87 (1.20-6.86) |
| time to hip fracture < 15 y[d] | 43/40 | 4.87 (1.81-13.1) |
| time to hip fracture ≥ 15 y[d] | 37/37 | 1.76 (0.69-4.46) |

Figure 10:
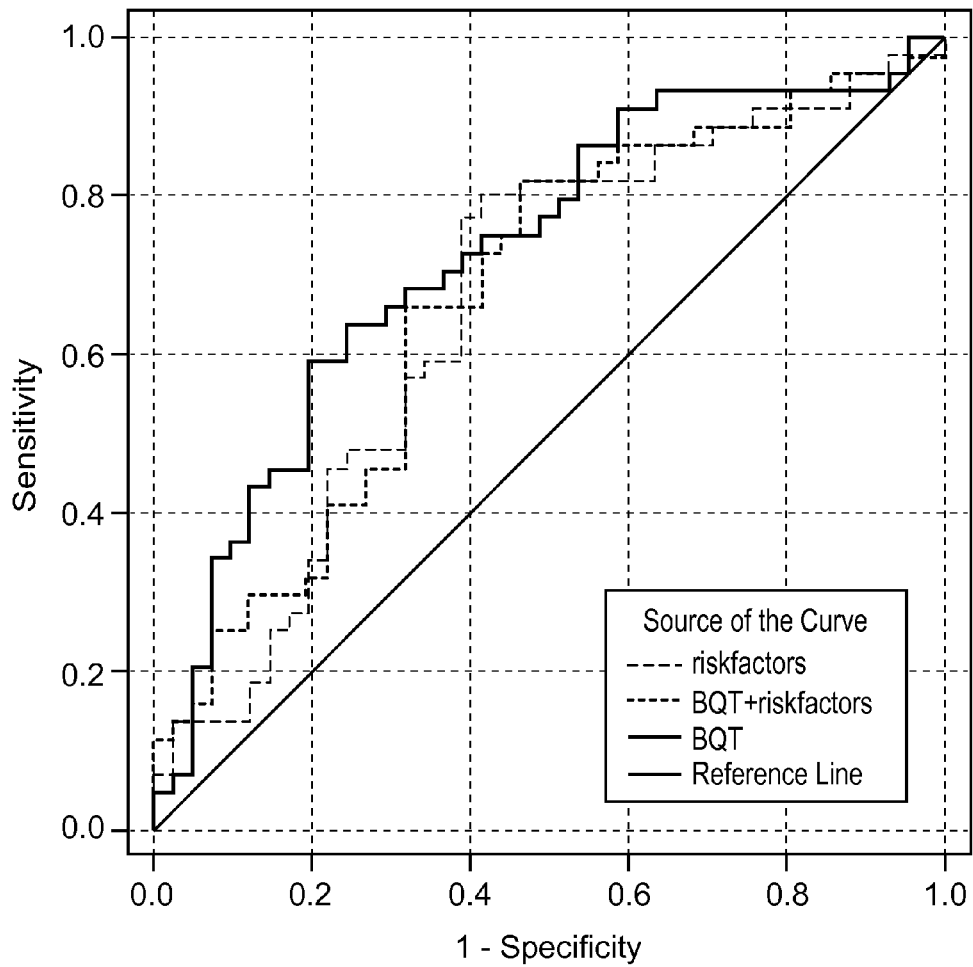
FIG. 10 is a graph showing areas under receiver operator characteristic curve for prediction models in hip fracture cases up to 15 years post nail collection and their matched controls.

[a]unconditional regression analysis adjusted for age at toenail collection
[b]BQT ® score ranges from 0 to 1. One standard deviation in BQT ® = 0.2
[c]time from toenail collection to hip fracture of case and its matched control; range is 3-20 y In a sub-group analysis that limited hip fracture cases to 15 years post nail collection (n=4483), the predictive ability of the assay improved, with an OR of 2.14 (p<0.01) and area under the curve (AUC) of 0.67 (0.56-0.77; FIG. 10). In combination with the clinical risk factors the figures for OR and AUC were 2.14 (95% CI 1.24-3.70) and 0.73 respectively. Using clinical risk factors alone an OR of 2.69 (95% CI 1.54-4.72) and an AUC of 0.66 was achieved. The use of analytical measurements significantly improved the model over risk factors alone (p=0.006). A comparison of the ROC curves is shown in FIG. 10.

What is claimed is:

1. A method for assessing risk of bone fracture of a bone of a mammal, the method comprising:
   a) conducting an assay to determine a characteristic of proteins in a nail obtained from a mammal by using Raman Spectroscopy to obtain Raman spectra of sulfur bonding at a depth between 30 and 70 μm into the nail and performing a multivariate spectral analysis (SA-MVA) on the Raman spectra, wherein the Raman spectra covers a spectral region between 300 cm$^{-1}$ and 1800 cm$^{-1}$;
   b) analyzing at least one bone-fracture risk factor associated with the mammal; and
   c) correlating results from steps (a) and (b), thereby assessing the risk of bone fracture of a bone of the mammal.

2. The method according to claim 1, wherein the Raman spectroscopy measures a peak selected from a group consisting of: a peak at about 510 cm$^{-1}$; a peak at about 621 cm$^{-1}$; and a peak at about 643 cm$^{-1}$.

3. The method according to claim 1, wherein the nail has been archived for a period of time.

4. The method according to claim 1, wherein the bone is a hip bone.

5. The method according to claim 1, wherein the bone-fracture risk factor is selected from a group consisting of: age, body mass index (BMI), smoking status, thyroid hormone use, diet, age at menopause, alcohol consumption, diagnosis of osteoporosis, and a combination thereof.

6. A method for assessing risk of bone fracture of a bone of a mammal, the method comprising:
   measuring changes in chemical composition of a clipped nail by using Raman Spectroscopy to obtain Raman spectra of sulfur bonding at a depth between 30 and 70 μm into the clipped nail and performing a multivariate spectral analysis (SA-MVA) on the Raman spectra, wherein the Raman spectra covers a spectral region between 300 cm$^{-1}$ and 1800 cm$^{-1}$; and
   comparing obtained Raman spectra to a set of reference spectra, thereby assessing the risk of bone fracture of a bone of the mammal.

7. The method according to claim 6, wherein the depth is at least 50 microns into the clipped nail.

8. The method according to claim 6, wherein changes in chemical composition of the clipped nail are changes in levels of sulfur bonding in proteins in the clipped nail.

9. The method according to claim 6, wherein the SA-MVA includes removal of spectral background features using a Fourier transform analysis.

10. The method according to claim 6, wherein the SA-MVA includes normalizing a peak height measurement using a reference peak height of a Raman feature that is invariant between normal and unhealthy subjects.

* * * * *